US012767949B2

(12) United States Patent
Mykhailiuk et al.

(10) Patent No.: US 12,767,949 B2
(45) Date of Patent: Oct. 20, 2026

(54) SELF-CLEAVING DNAzymes AND SELECTION PROCESS

(71) Applicant: TECHNISCHE UNIVERSITÄT MÜNCHEN, Munich (DE)

(72) Inventors: Volodymyr Mykhailiuk, Munich (DE); Hendrik Dietz, Haar (DE)

(73) Assignee: TECHNISCHE UNIVERSITÄT MÜNCHEN, Munich (DE)

( * ) Notice: Subject to any disclaimer, the term of this patent is extended or adjusted under 35 U.S.C. 154(b) by 0 days.

(21) Appl. No.: 19/364,843

(22) Filed: Oct. 21, 2025

(65) Prior Publication Data

US 2026/0078374 A1 Mar. 19, 2026

Related U.S. Application Data

(63) Continuation of application No. PCT/EP2024/060735, filed on Apr. 19, 2024.

(30) Foreign Application Priority Data

Apr. 21, 2023 (EP) .................................... 23169206

(51) Int. Cl.
*C12N 15/113* (2010.01)
*C12Q 1/6869* (2018.01)

(52) U.S. Cl.
CPC .......... *C12N 15/113* (2013.01); *C12Q 1/6869* (2013.01); *C12N 2310/127* (2013.01)

(58) Field of Classification Search
None
See application file for complete search history.

(56) References Cited

FOREIGN PATENT DOCUMENTS

| | | | |
|---|---|---|---|
| EP | 2207474 | B1 | 8/2018 |
| EP | 3516055 | | 12/2021 |
| WO | 2018054571 | A1 | 3/2018 |
| WO | 2021165528 | | 8/2021 |

OTHER PUBLICATIONS

Gu, Hongzhou, et al. "Small, highly active DNAs that hydrolyze DNA." Journal of the American Chemical Society 135.24 (2013): 9121-9129.

International Search Report issued Jul. 3, 2024 in PCT/EP2024/060735, 6 pages.

Zhang, Canyu, et al. "New DNA-hydrolyzing DNAs isolated from an ssDNA library carrying a terminal hybridization stem." Nucleic Acids Research 49.11 (2021): 6364-6374.

Bai, H., Liu, L., An, K., Lu, X., Harrison, M., Zhao, Y., Yan, R., Lu, Z., Li, S., Lin, S., Liang, F., & Qin, W. (2020). CRISPR/Cas9-mediated precise genome modification by a long ssDNA template in zebrafish. BMC Genomics, 21(1), 1-12.

Breaker RR. DNA enzymes. Nat Biotechnol. 1997;15(5):427-31.

Breaker, R. R. & Joyce, G. F. A DNA enzyme that cleaves RNA. Chem Biol 1, 223-229 (1994).

Carmi, N., Shultz, L. A. & Breaker, R. R. In vitro selection of self-cleaving DNAs. Chem Biol 3, 1039-1046 (1996).

Chandra, M., Sachdeva, A. & Silverman, S. K. DNA-catalyzed sequence-specific hydrolysis of DNA. Nat Chem Biol 5, 718-720 (2009).

Gerling T. et al. 2015 Dynamic DNA devices and assemblies formed by shape-complementary, non-base pairing 3D components. Science. 6229, 1446-1452.

Lee, Y. et al. DNA-Catalyzed DNA Cleavage by a Radical Pathway with Well-Defined Products. J Am Chem Soc 139, 255-261 (2017).

Pumm, AK., Engelen, W., Kopperger, E et al. 2022. A DNA origami rotary ratchet motor. Nature 607, 492-498.

Quadros, R. M., Miura, H., Harms, D. W., Akatsuka, H., Sato, T., Aida, T., Redder, R., Richardson, G. P., Inagaki, Y., Sakai, D., Buckley, S. M., Seshacharyulu, P., Batra, S. K., Behlke, M. A., Zeiner, S. A., Jacobi, A. M., Izu, Y., Thoreson, W. B., Urness, L. D., . . . Gurumurthy, C. B. (2017). Easi-CRISPR: A robust method for one- step generation of mice carrying conditional and insertion alleles using long ssDNA donors and CRISPR ribonucleoproteins. Genome Biology, 18(1), 1-15.

Sheppard TL, Ordoukhanian P, Joyce GF. A DNA enzyme with N-glycosylase activity. Proc NatlAcadSci USA. 2000;97 (14):7802-7.

Sigl, C., Willner, E.M., Engelen, W. et al. 2021. Programmable icosahedral shell system for virus trapping. Nat. Mater. 20, 1281-1289.

Velez, T. E. et al. Systematic Evaluation of the Dependence of Deoxyribozyme Catalysis on Random Region Length. ACS Comb Sci 14, 680-687 (2012).

Wang, M. et al. In vitro selection of DNA-cleaving deoxyribozyme with site-specific thymidine excision activity. Nucleic Acids Res 42, 9262-9269 (2014).

Xiao, Y., Wehrmann, R. J., Ibrahim, N. A. & Silverman, S. K. Establishing broad generality of DNA catalysts for site-specific hydrolysis of single-stranded DNA. Nucleic Acids Res 40, 1778-1786 (2012).

Zhang, Qiao, et al. "Catalytic DNA-Assisted Mass Production of Arbitrary Single-Stranded DNA." Angewandte Chemie 135.5 (2023): e202212011.

*Primary Examiner* — Juliet C Switzer
*Assistant Examiner* — Brian Ellis Young
(74) *Attorney, Agent, or Firm* — Greenberg Traurig, LLP; Wei Zhang; David Mata

(57) ABSTRACT

The present invention provides a novel in vitro method of selecting DNAzymes with self-cleaving activity, novel DNAzymes and their use for the production of single stranded DNA.

19 Claims, 7 Drawing Sheets

Specification includes a Sequence Listing.

5' Cy3-TTTTTTTTGCAGATAATGGGTCGTGTACGCCTCGTCTTATCGGTTATCTATTATCT-Cy5 3'

| | Found products of 12-11 cleavage | Expected Mass | Found Mass |
|---|---|---|---|
| 1 | 5'-TTTTTTTTGCAGATAATG-**OH**-3' | 5506.9 | 5508.9 |
| 2 | 5'-**P**-GGTCGTGTACGCCTCGTCTTATCGGTTATCTATTATCTGC-3' | 12300.3 | 12305.8 |

SELF-CLEAVING DNAzymes AND SELECTION PROCESS

RELATED APPLICATIONS

This application is a continuation of International Application No. PCT/EP2024/060735, filed Apr. 19, 2024, which claims priority to European Patent Application No. 23169206.2, filed Apr. 21, 2023, the entire contents of all are incorporated herein by reference for all purposes.

SEQUENCE LISTING

The instant application contains a Sequence Listing which has been submitted electronically in XML format and is hereby incorporated by reference in its entirety. Said XML copy, created on Feb. 5, 2026, is named 234916-717301_SL and is 56,554 bytes in size.

BACKGROUND OF THE INVENTION

Biomolecular and therapeutic applications feed the demand for development of progressively more sophisticated and complex DNA origami. DNA origami is a technique that allows fabrication of nanostructures of designer-defined shape and dimensions at nanometer scale relying on the programmability and self-assembly properties of DNA. In recent years, this motivated a shift towards high precision DNA origami designs that include functional domains (Gerling T. et al., 2015) and allow higher order assemblies (Sigl, C. et al., 2021; Pumm, A K. et al., 2022).

EP3516055B1 describes a phage-mediated method of scalable biotechnological production of single-stranded DNA (ssDNA) using self-cleaving DNA sequences.

DNAzymes are DNA molecules that form structures capable of catalyzing chemical reactions (Breaker et al., 1997). There are DNAs that catalyze self-processing reactions (Carmi et al., 1996). Such DNAzymes can be harnessed to create DNA constructs that become modified based on their inherent catalytic activities when exposed to specific reaction conditions. For example, there are engineered self-cleaving DNAzymes that employ oxidation (Carmi et al., 1996), depurination (Sheppard et al., 2000), or hydrolysis (see e.g., Chandra et al., 2009) mechanisms that have been created by using various directed evolution strategies.

Two classes of engineered self-cleaving DNAzymes were described that hydrolyze DNA with high speed and sequence specificity (Gu et al., 2013). One such DNAzymes, named I-R3, carries a small catalytic core composed of 17 nucleotides flanked by either 1 or 2 double stranded substructures. Representatives of this DNAzyme class exhibit an observed rate constant ($k_{obs}$) for DNA hydrolysis of ~1 $min^{-1}$ (half-life of ~40 s) when incubated at near neutral pH and in the presence of millimolar concentrations of $Zn^{2+}$. This DNAzyme cleaves the phosphoester bond between the 3' oxygen and the phosphorus center of an ApA linkage to yield a 3' cleavage fragment with a 5' phosphate group.

When used in the production of ssDNA, I-R3 DNAzyme produces target ssDNA strands with constant terminal sequence motifs originating from the DNAzyme sequence itself ("scar" sequence AG at the 5' and an ACGTTGA at the 3'). However, an attempt to accommodate the complement sequences for 7 nt long 3' motif would introduce multiple long repeats in a DNA origami scaffold strand. This may compromise the addressability of DNA during structure assembly reaction resulting in low or no yield and/or formation of misfolded structures. Alternatively, leaving ssDNA overhangs at the breakpoints would be incompatible with functional domains that use blunt-ended stacking interactions for higher order assemblies. Furthermore, homology-directed repair (HDR) applications may be adversely affected by non-homologous ssDNA overhangs.

Qiao Zhang et al., 2022 describes a II-R2/3 DNAzyme which shows full generality of site-specific DNA cleavage while also removing the overhang motif. However, the noticeably larger core of II-R2/3 (59 nt) compared to that of IR3 (40 nt), together with the incomplete cleavage yield (capped at around 90%) as seen for II-R2/3 significantly compromises the utility of II-R2/3 for successful mass-production of multiple (>30) arbitrary ssDNA needed for DNA origami.

Most of reported in vitro selection strategies for DNAzymes can be assigned to 3 main groups. The first group cover the very first discovered DNA and RNA self-cleaving DNAzymes designed to performed cleavage within a constant sequence at some distance from to the catalytic core (Breaker, R. R. et al., 1994; Carmi, N. et al., 1996). The second group employs two constant flanking sequences as binding arms to aim the DNAzyme core towards predetermined region of the substrate (Chandra, M. et al., 2009; Lee, Y. et al.; 2017). In vitro selection methods based on circularization of DNA library (Gu, H. et al., 2013; Zhang C. et al., 2021) make up the third group. Taking advantage of freedom of choice for the cleavage site within evolving catalytic core, this approach yielded one of the most active DNA-cleaving DNAzymes.

Despite of the abundance of reported methods, none allows to deliberately produce a scar-free self-cleaving DNAzyme from a random space. Available approaches either rely on an already existing DNAzyme that possesses desired cleavage site (Qiao Zhang et al., 2022) or provide selection pressure on the cleavage site within the known substrate sequence (Xiao Y. et al., 2012).

Object

There is still a demand for improved DNAzymes minimizing the "scars" at the 5' and 3' ends of ssDNA while maintaining high cleavage efficiency. Further, there is still a demand for a novel selection process for DNAzymes allowing for selection of DNAzymes from random spaces independently of a specific cleavage mechanism, an existing DNAzyme and/or a specific substrate sequence.

SUMMARY OF THE INVENTION

In one aspect, the invention provides a method, e.g., an in vitro method, for selecting a DNAzyme with self-cleaving activity, the method comprising:

(a) providing a plurality of single-stranded DNA strands,
  wherein each single-stranded DNA strand comprises a core region of random nucleotides flanked by a constant region 1 at its 5' end and a constant region 2 at its 3' end, and
  wherein each constant region comprises a primer binding part;

(b) subjecting the plurality of single-stranded DNA strands to self-cleaving conditions;

(c) isolating cleavage products 2, and optionally isolating cleavage products 1,
  wherein the cleavage products 2 comprise the constant region 2, the core region, and wherein the cleavage products 2 comprise a DNA self-cleaving activity, and wherein the cleavage products 1 comprise the constant region 1, preferably wherein cleavage of the single-stranded DNA strands occurred between the catalytic core and the constant region 1, or wherein the cleavage products 2 comprise the constant region 2, the core region, and a part of constant region 1, and wherein the cleavage products 2 comprise a DNA self-cleaving activity, and wherein the cleavage products 1 comprises the remaining part of the constant region 1, preferably wherein cleavage of the single-stranded DNA strands occurred within the constant region 1;

(d) producing complements of the cleavage products 2;

(e) optionally separating the complements of the cleavage products 2;

(f) ligating the 3' end of the complements of the cleavage products 2 to complements of the cleavage products 1, thereby obtaining complements of single-stranded DNA strands of step (a) with the DNA self-cleaving activity;

(g) optionally separating the complements of the single-stranded DNA strands;

(h) amplifying the complements of the single-stranded DNA strands thereby obtaining DNA strands comprising the DNA self-cleaving activity;

(i) optionally separating the DNA strands comprising the self-cleaving activity;

(j) optionally subjecting the DNA strands comprising the self-cleaving activity to an error prone (EP-PCR) step; and (k) optionally subjecting the DNA strands comprising the self-cleaving activity of step (h), optionally of steps (i) or (j), to one or more rounds of steps (b)-(h), and optionally to one or more rounds of steps (i) and/or (j).

In a further aspect, the invention relates to a DNAzyme obtainable by the method according to the invention, preferably wherein the DNAzyme comprises a self-cleaving activity between the catalytic core and the constant region 1 or within constant region 1.

In a further aspect, the invention relates to a DNAzyme comprising the following sequence:

(SEQ ID NO: 1)

5'-$N^{\&}$ G $Y^{\$}$ $Y^{\#}$ GT $N^{\$}$ $Y^{\#}$ ACGC $Y^{\#}$ $Y^{\$}$ YGTCTTATCGGTT $Y^{\$}$ $Y^{\$}$ $N^{\#}$ N-3', wherein A is a nucleotide with the base adenine, C is a nucleotide with the base cytosine, G is a nucleotide with the base guanine, T is a nucleotide with the base thymidine, N is independently A, C, G, or T, Y is independently C or T, $ is independently preferably T, # is independently preferably C,

& is independently preferably G, and wherein the DNAzyme comprises a self-cleaving activity, optionally wherein an additional nucleotide N# is included between nucleotide position 29 and 30 of SEQ ID NO: 1, wherein the numbering of nucleotides is from 5' to 3' direction of SEQ ID NO: 1.

In a further aspect, the invention relates to the use of the DNAzyme of the invention in the production of single stranded DNA molecules, preferably wherein the single stranded DNAzyme is used in DNA nanotechnology and/or wherein the single stranded DNAzyme is used in genome editing.

BRIEF DESCRIPTION OF THE FIGURES

FIG. 3A. Fraction cleaved after 24 hours of incubation; FIG. 3B. Progress of the cleavage reaction over time; FIG. 3C. The cleavage yield vs time data fitted to the pseudo-first order kinetics model.

FIG. 5A: Sequence of the double-labeled oligonucleotide of 12-11 DNAzyme, the catalytic core is underlined and cleavage site is marked; FIG. 5B: Assigned DMS ladder of double-labeled 12-11 DNAzyme and its cleavage product (1 and 2) resolved with 15% PAGE and imaged by excitation of Cy3 and Cy5 terminal tags; FIG. 5C: Detected by ESI-MS products of 12-11 cleavage.

DETAILED DESCRIPTION

Figure 1:
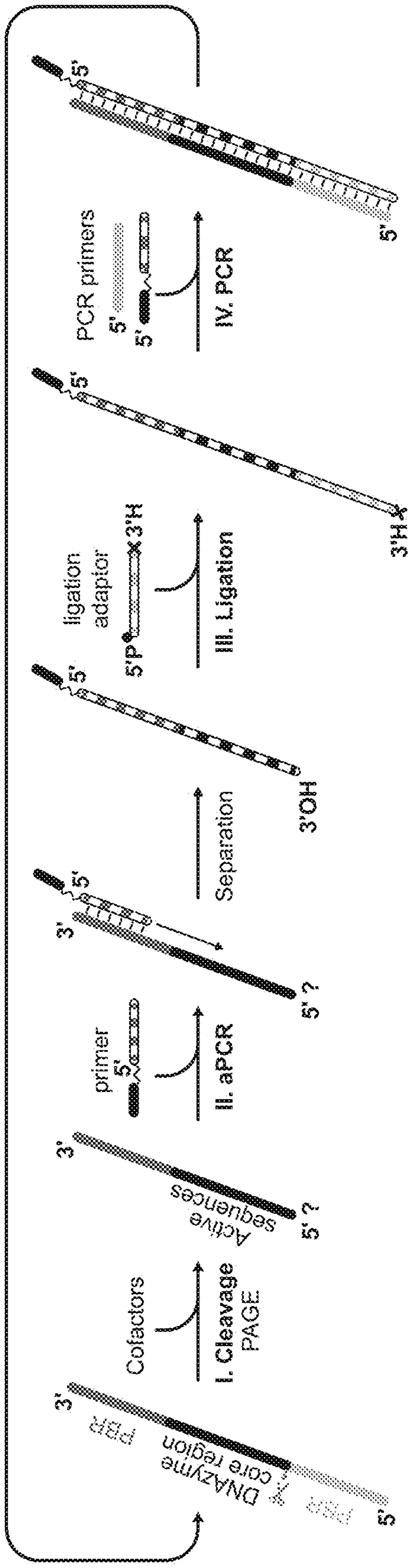
FIG. 1 shows a general scheme of the novel in vitro selection process for self-cleaving DNAzymes. The in vitro selection procedure can be split in four major steps: the cleavage reaction (I), generation of the reverse complement of the active fraction (II), the restoration of 5' constant sequence by ligation (III), PCR amplification (IV). The cleavage site can be selected within 5' constant sequence including the cleavage between the 5' constant sequence and the core (the latter indicated by the scissor symbol). The sequence of the ligation adaptor must be designed accordingly. To obtain a robust cleaver regardless of its mode of action, a strategy was implemented that permitted any catalysis type of cleavage as long as it led to DNA break at the intended site. Therefore, instead of proceeding to work with enriched pool directly, the sequence data was transferred into a new DNA strand in the form of the reverse complement.

Unless defined otherwise, all technical and scientific terms used herein have the same meaning as commonly understood by those of ordinary skill in the art to which this invention pertains.

The term "comprising" or "comprises" as used herein means "including, but not limited to". The term is intended to be open-ended, to specify the presence of any stated features, elements, integers, steps, or components, but not to preclude the presence or addition of one or more other features, elements, integers, steps, components, or groups thereof. The term "comprising" or "comprises" thus includes the more restrictive terms "consisting of" and "consisting essentially of". In one embodiment, the term "comprising" or comprises" as used throughout the application and in particular within the claims may be replaced by the term "consisting of" or "consisting essentially of".

The terms "a" and "an" and "the" and similar references in the context of describing the invention (especially in the context of the following claims) are to be construed to cover both the singular and the plural, unless otherwise indicated herein or clearly contradicted by context. For example, the term "a constant region" includes a plurality of constant regions, including mixtures thereof. Where the plural form is used for compounds, salts, and the like, this is taken to mean also a single compound, salt, or the like.

In the context of the present disclosure, the term "DNA" refers to deoxyribonucleic acid composed of a single-strand of monomeric units called nucleotides, wherein each nucleotide is composed of a nitrogen-containing nucleobase, a 2-deoxyribose sugar moiety, and a phosphate group, wherein the individual nucleotides are linked in the single-strand by a phosphate group linking the OH group in position 5' of a 2-deoxyribose sugar moiety to the OH group in 3' of a neighboring 2-deoxyribose sugar moiety. In particular embodiments, the nitrogen-containing nucleobases are independently selected from cytosine [C], guanine [G], adenine [A] and thymine [T] In particular embodiments, one or more of the nucleobases are non-canonical bases, in particular a non-canonical base selected from the list of: a modified adenosine, in particular N6-carbamoyl-methyladenine or N6-methyadenine; a modified guanine, in particular 7-deazaguanine or 7-methylguanine; a modified cytosine, N4-methylcytosine, 5-carboxylcytosine, 5-formylcytosine, 5-glycosylhydroxymethylcytosine, 5-hydroxycytosine, or 5-methylcytosine; a modified thymidine, in particular a-glutamyl thymidine or a-putrescinyl thymine; a uracil or a modification thereof, in particular uracil, base J, 5-dihydroxypentauracil; or 5-hydroxymethyldeoxyuracil; deoxyarchaeosine and 2,6-diaminopurine. A stretch or part of a single-strand of DNA may interact with a complementary stretch of DNA by interaction of complementary nucleobases to form a duplex, wherein cytosine and guanine, and adenine and thymine, are complementary to each other, respectively, by forming two (A/T) and three (G/C) hydrogen bonds between the nucleobases. A duplex may be formed by two single-strands of DNA that are fully complementary to each other, as in the case of genomic DNA, or by single-strands of DNA that are partially complementary to each other, including situations, where one single-strand of DNA is partially complementary to two or more other single-stranded DNA strands. A duplex may also be formed by two fully or partially self-complementary stretches of one single stranded of DNA resulting in the formation of, e.g., a hairpin, a loop, a hybridization stem or higher order motives such as triplex DNA, pseudoknots or kissing hairpins.

In the context of the present disclosure, the term "DNAzyme", also called "Deoxyribozymes", "DNA enzymes", or "catalytic DNA", are DNA oligonucleotides that are capable of performing a specific chemical reaction. The specific chemical reaction might be a cleavage, such as a self-cleavage. There is little evidence for naturally occurring DNAzymes.

Without being bound to any theory, this is most probably due to limited functional groups compared to proteins and a limited physical flexibility of the natural double-stranded conformation. Thus, DNAzymes are usually single stranded optionally with self-complementary regions awarding a specific conformation which might in certain cases influence their activity.

DNAzymes are produced through a high-throughput in vitro selection technique from a pool of many random DNA spaces that can be screened for a specific chemical reaction or catalytic activity. By applying selective pressure through adaptation of the selection conditions during the selection process, e.g., incubation time, salt concentration, pH and the presence of cofactors, a DNA sequence can be selected according to a specific chemical reaction, e.g., hydrolytic cleavage, and/or to a specific position. The selection process can be further enhanced by introducing genetic alterations into the DNA sequences either in the initial pool of DNA sequences or after several rounds of selection to evolve DNA strands with increased activity which will dominate the pool after multiple selection steps. Usually, genetic alterations are introduced through genetic recombination or point mutations. For introducing point mutations, the pool can be amplified using error-prone PCR (EP-PCR) to produce many different strands of various, random, single mutations.

The "pseudogene nucleic acid" as used herein is a nucleic acid that comprises at least one target DNA oligo- or polynucleotide sequence and two self-cleaving DNA sequences flanking each target DNA oligo- or polynucleotide sequence. Preferably, the pseudogene nucleic acid comprises one or many target DNA oligo- or polynucleotide sequences, such as two, three, four or more than about 50 target DNA oligo- or polynucleotide sequences.

Cleaving activity" as used herein is represented by the observed rate constant ($k_{obs}$) and the final yield of the self-cleavage reaction ($Y_{max}$) values. The reaction yield (Y) is the yield at a given moment of time since the start of the reaction is calculated as the proportion of the DNAzyme molecules that underwent self-cleavage. The $k_{obs}$ is calculated by fitting the reaction yield versus time (t) to a pseudo-first order kinetic model: $Y=Y_{max}(1-e^{-kobs*t})$. The final yield of the reaction is preferably determined from the proportion of cleaved DNAzyme molecules after prolonged reaction time Y, preferably within 24 hours from the beginning of a cleavage reaction, e.g., at one or more timepoints after 1, 2, 3, 5, 7, 9, 10, 15, 20 or 24 hours from the beginning of a cleavage reaction, more preferably after 24 hours from the beginning of a cleavage reaction.

Figure 2:
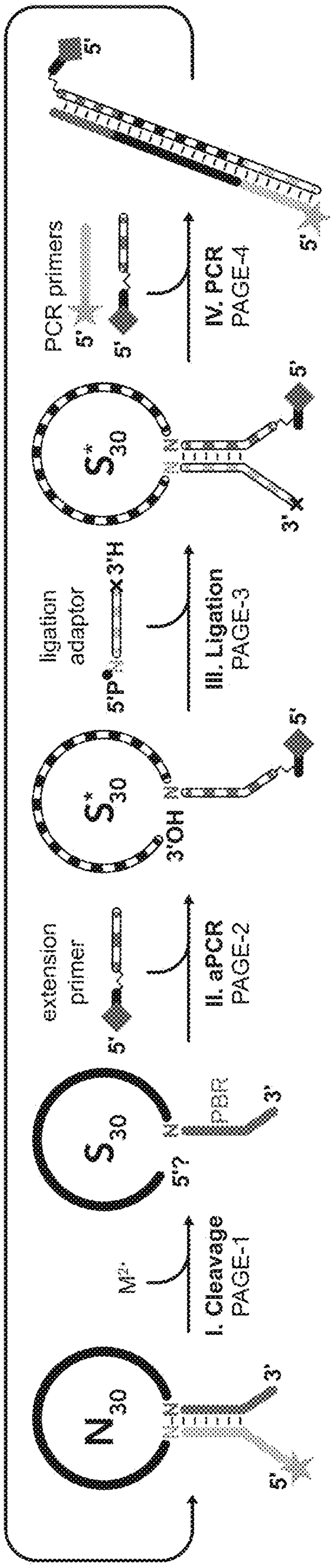
FIG. 2 shows a specific embodiment of the novel in vitro section process for self-cleaving DNAzymes that places evolutionary pressure on the cleavage of the 1st nucleotide of the constant region 1 at the 5' end (light grey). The initial DNAzyme library sequence was constructed in a rather conventional fashion—the randomized core region (black) was flanked by two constant regions 1 and 2 (grey). The later were partially complementary to each other forming a terminal hybridization stem for the core loop and thus mimicking the DNAzyme cassette set up. The unhybridized parts served as primer binding regions for the amplification steps. The initial library consisted of four sub-libraries. Each of them featured one of four possible base pairs at the preselected cleavage site with the intent to avoid bias towards one fixated nucleotide at the start of selection. Aiming to produce a DNAzyme more compact than already available I-R3 and 11-R2/3, we settled with a $N_{32}$ core region.
Figure 3A:
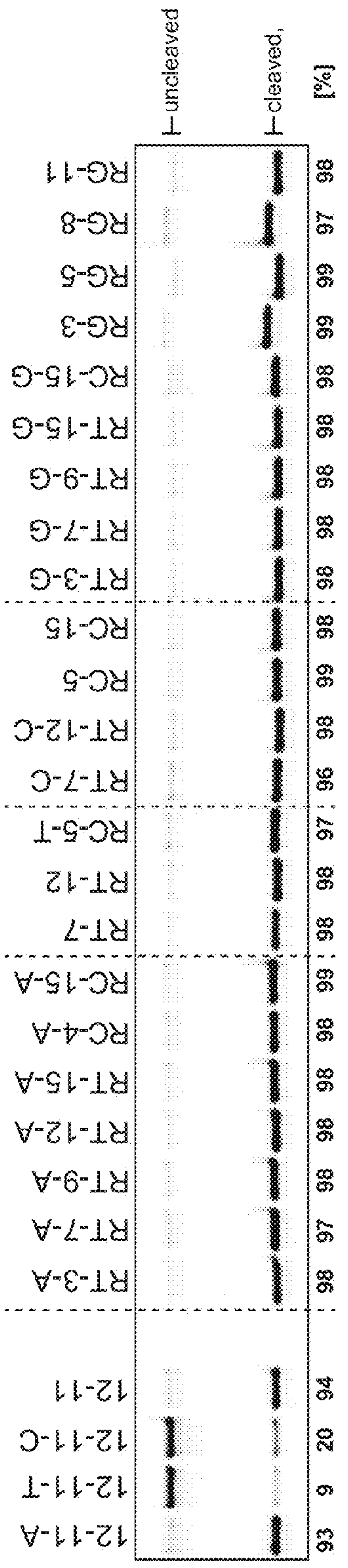
FIGS. 3A-3C show the activity of parent DNAzyme 12-11 and its reselected variants.
Figure 3B:
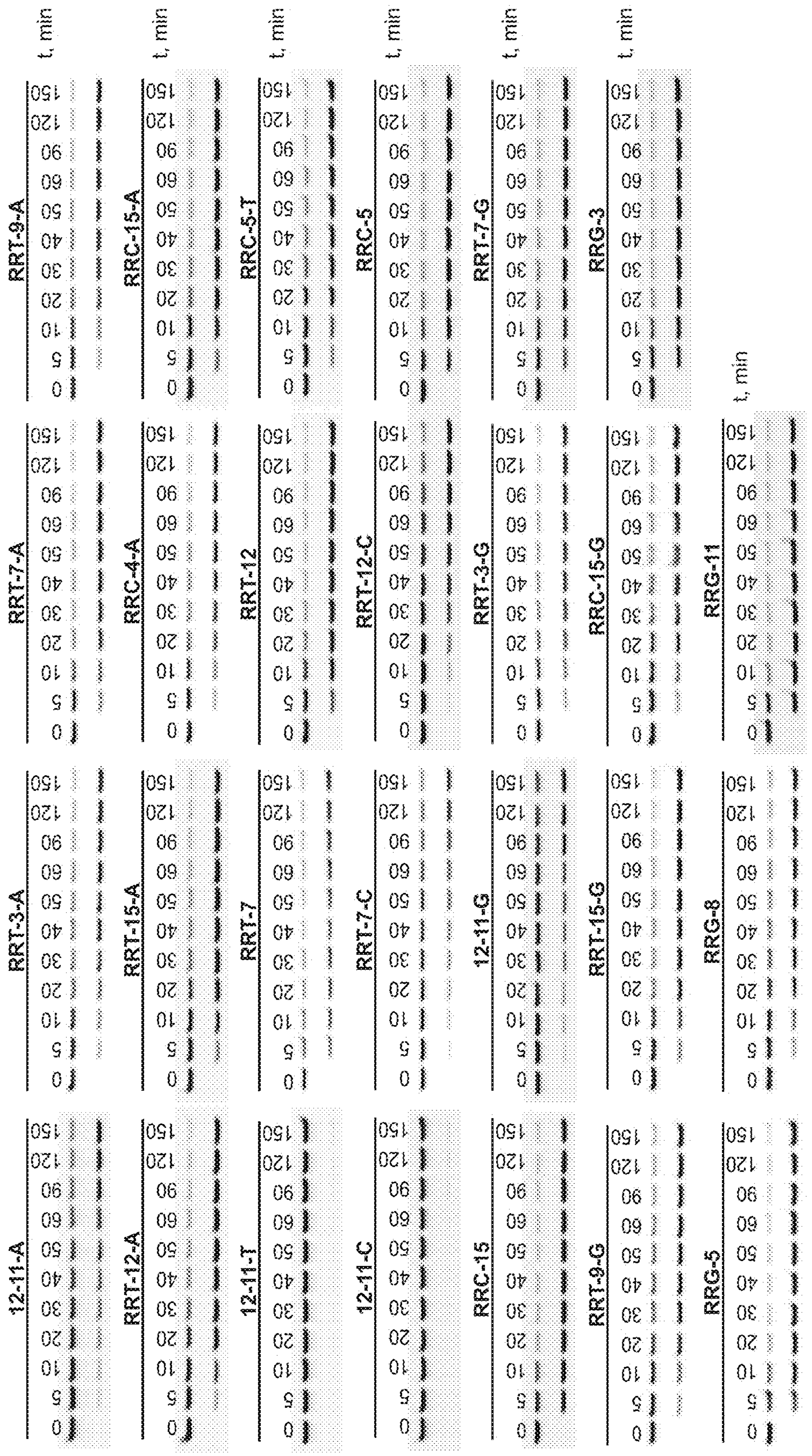
Figure 3C:
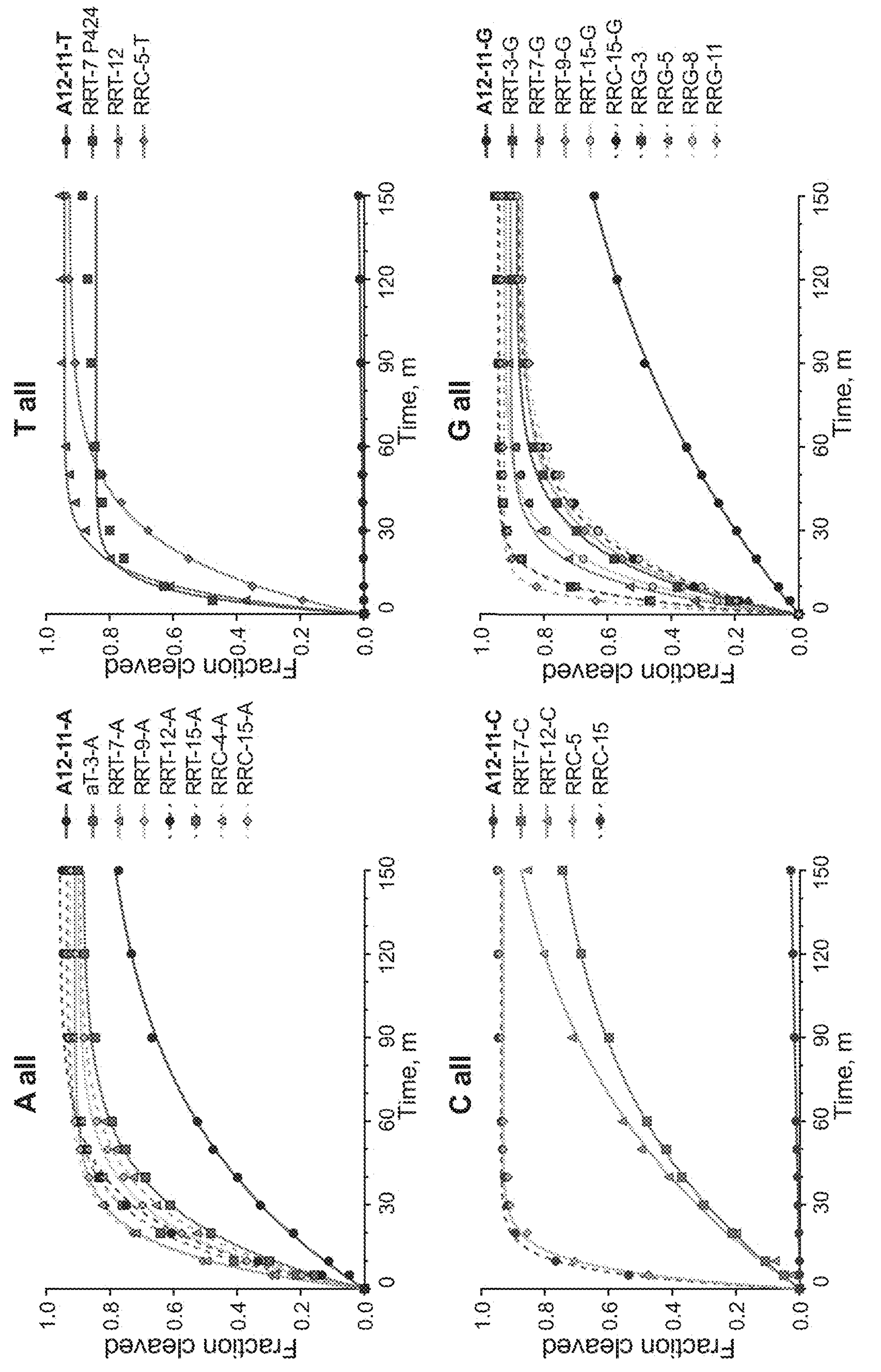
Figure 4:
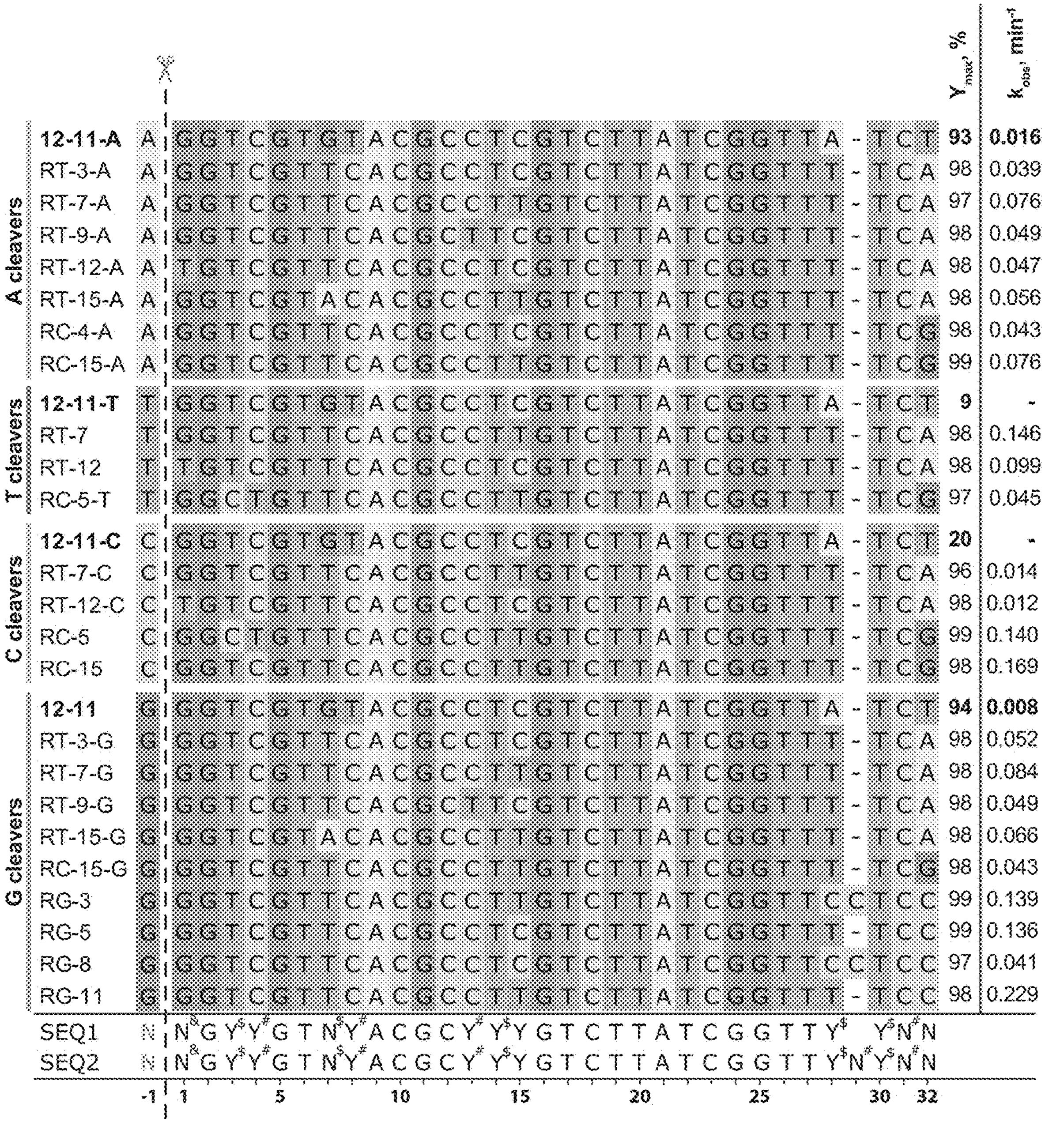
FIG. 4 shows the sequences of tested self-cleaving DNAzymes and activity data for 12-11 DNAzyme and selected variants performing self-cleaving reaction in context of one of the four nucleotides at the cleavage site.
Figures 5A, 5B, 5C:
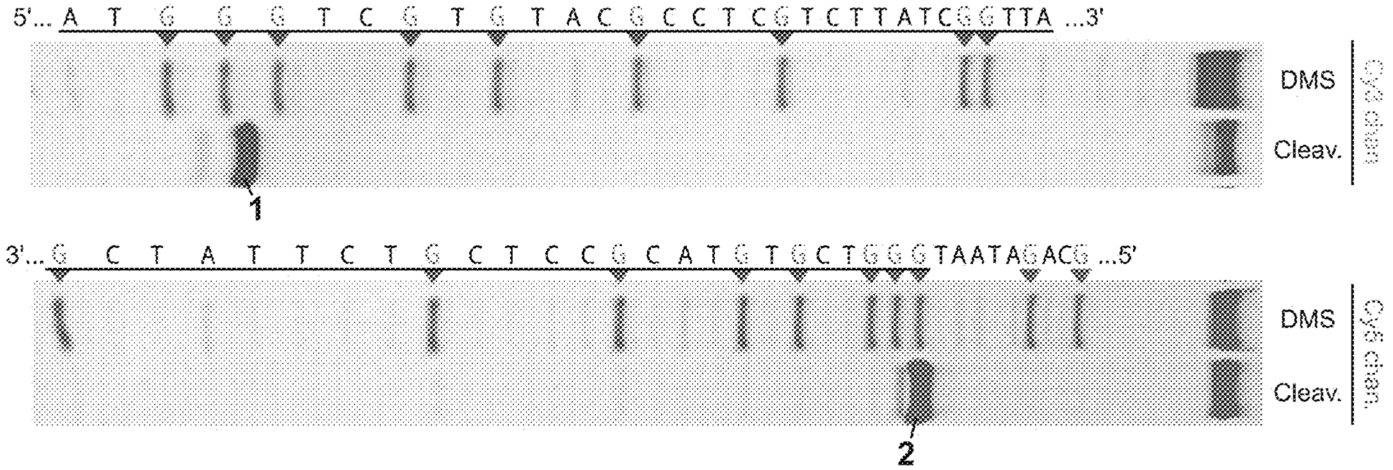
FIGS. 5A-5C Confirmation of the cleavage site of 12-11 DNAzyme by DMS assay and mass spectrometry analysis.

The inventors designed a novel in vitro selection method that places evolutionary pressure on the cleavage site location (FIGS. 1 and 2). The proposed in vitro selection procedure can be split in four major steps (FIG. 1): the cleavage reaction (I), generation of the reverse complement of the active fraction (II), the restoration of 5' constant sequence by ligation (III), PCR amplification (IV). Traditionally, the capture step for active DNAzyme sequences exploits a reaction with a specific chemical group within the expected products of catalysis (Wang et al., 2014). A DNA cleaving reaction can unfold following different catalytic pathways giving multitude of possible terminal groups at the cleavage site (Xiao et al., 2012; Lee et al., 2017). Often this allows to isolate a sequence catalyzing a reaction in a specific mode. With the ambition to obtain a robust cleaver regardless of its mode of action, the inventors implemented a strategy that permitted any catalysis type as long as it led to DNA break at the intended site. Therefore, instead of proceeding to work with an enriched pool directly, the sequence data was transferred into a new DNA strand in the form of a reverse complement. The DNA which was isolated after cleavage served as a template for primer extension via the 3' constant sequence. The reaction yield indirectly indicated the library cleavage efficiency in the current round. Thus, it was used to follow the enrichment progress through selection and to adjust the incubation time for the cleavage reaction. Most importantly, the DNA strand generated after primer extension was always terminated with a 3'-hydroxyl group regardless of the DNAzymes original mode of action. This was readily used to perform recovery of the full library structure by adaptor ligation. Subsequently, the full-sized ssDNA pool for next round was produced using PCR amplification. The selection procedure was repeated until the library became sufficiently enriched.

The new selection approach allowed to successfully evolve novel self-cleaving DNAzymes that work robustly with high cleavage yields, that are very compact (31 nucleotides (nt)/32 nt) and thus reduce the amount of waste DNA during production of ssDNA, and that are insensitive to the upstream DNA sequence context, meaning they produce scar-free 3'-end of target sequence.

In one aspect, the invention relates to a method, e.g., an in vitro method, for selecting a DNAzyme with self-cleaving activity, the method comprising:

(a) providing a plurality of single-stranded DNA strands,
 wherein each single-stranded DNA strand comprises a core region of random nucleotides flanked by a constant region 1 at its 5' end and a constant region 2 at its 3' end, and
 wherein each constant region comprises a primer binding part;
(b) subjecting the plurality of DNA strands to self-cleaving conditions;
(c) isolating cleavage products 2, and optionally isolating cleavage products 1,
 wherein the cleavage products 2 comprise the constant region 2, the core region, and
 wherein the cleavage products 2 comprise a DNA self-cleaving activity, and
 wherein the cleavage products 1 comprise the constant region 1,
 preferably wherein cleavage of the single-stranded DNA strands occurred between the catalytic core and the constant region 1,
 or
 wherein the cleavage products 2 comprise the constant region 2, the core region, and a part of constant region 1, and
 wherein the cleavage products 2 comprise a DNA self-cleaving activity, and
 wherein the cleavage products 1 comprises the remaining part of the constant region 1,
 preferably wherein cleavage of the single-stranded DNA strands occurred within the constant region 1;
(d) producing complements of the cleavage products 2;
(e) optionally separating the complements of the cleavage products 2;
(f) ligating the 3' end of the complements of the cleavage products 2 to complements of the cleavage products 1, thereby obtaining complements of single-stranded DNA strands of step (a) with the DNA self-cleaving activity;
(g) optionally separating the complements of the single-stranded DNA strands;
(h) amplifying the complements of the single-stranded DNA strands thereby obtaining DNA strands comprising the DNA self-cleaving activity;
(i) optionally separating the DNA strands comprising the self-cleaving activity;
(j) optionally subjecting the DNA strands comprising the self-cleaving activity to an error prone (EP-FCR) step; and
(k) optionally subjecting the DNA strands comprising the self-cleaving activity of step (h), optionally of steps (i) or (j), to one or more rounds of steps (b)-(h), and optionally to one or more rounds of steps (i) and/or (j).

In one embodiment, steps (a)-(k) are consecutive steps.

In one embodiment the plurality of single-stranded DNA strands in step (a) may be further divided in sub-pools. For example, the plurality of single-stranded DNA strands may be further divided in sub-pools wherein each pool features one of four possible nucleotides A, T, G or C at the preselected cleavage site with the intent to avoid bias towards one fixated nucleotide at the start of selection.

In one embodiment, each single-stranded DNA strand in step (a), preferably in the first round of selection, consists of a core region of random nucleotides flanked by a constant region 1 at its 5' end and a constant region 2 at its 3' end.

The number of nucleotides in the core region of the single-stranded DNA strands in step (a) may be user defined may comprise any number of nucleotides. Setting the number as short as possible may be preferred as long as the cleavage activity is not compromised, particularly for a selection process which aims at selecting DNAzymes to produce ssDNA as the amount of waste DNA can be largely reduced during the production process which save costs. In one embodiment, the core region of the single-stranded DNA strands in step (a) comprises about 20-100 nucleotides, or about 25-50 nucleotides, or about 30-40 nucleotides, or about 32-35 nucleotides. In one embodiment, a nucleotide position of the core region is independently represented by any nucleotide (N).

In the context of the present disclosure, the term "catalytic core region" of DNAzyme refers to a unique nucleotide sequence that exhibit certain catalytic capabilities, wherein each nucleotide position is composed of a nucleotide with the identity conserved to a different degree. In one embodiment, 19 out of 31 nucleotides of the catalytic core region are highly conservative in their identity and sequence context. In one embodiment, a nucleotide position of the catalytic core region is independently represented by a pyrimidine (Y). In one embodiment, a nucleotide position of the catalytic core region is independently represented by any nucleotide (N). The catalytic core region is the subject of directed evolution (in vitro selection) towards certain catalytic capabilities. For example, at the start of the in vitro selection process, the core region is represented by random nucleotides and consists as a part of a plurality of sequences prepared synthetically by methods that are known to the person skilled in the art including but not limited to solid phase synthesis, enzymatic DNA synthesis, enzymatic ligation. The incorporation frequency of nucleotides for each nucleotide position can be completely flexible and tuned by the designer. For example, the core region of the initial library can be completely randomized or contain positions where one of the nucleotides has higher incorporation chance. Also stretches of nucleotides can be constrained to constant predefined identities, such can form loops or hairpins structures inside of the core region. In one embodiment, all the positions of core region in initial pool had even a chance for incorporation of A, T C or G nucleotide. In one embodiment, each position of the core region of initial library had 70% incorporation chance of nucleotide with defined identity. The usage of unnatural and modified nucleotides in synthesis of initial library is also possible in order to expand chemical repertoire of catalysis or to expand DNAzyme properties.

The term "random nucleotides" as used herein, refers to a random composition of nucleotides, preferably A, T, G or C, a random sequence of the individual nucleotides and/or to a random nature of the individual nucleotides including but not limited to non-canonical bases as described herein or sugar moiety modifications such as 2'. Basically, the modifications of the individual nucleotides should not interfere with the base pairing and/or phosphodiester bonding properties between single nucleotides.

In one embodiment, all single-stranded DNA strands in step (a) comprise the same constant region 1 and the same constant region 2. Preferably, constant region 1 and constant region 2 are different which allow for different primers to bind to constant region 1 or to constant region 2 and/or for formation of complementary sub-parts. For example, the constant regions 1 of the single-stranded DNA strands in step (a) comprise a part which is complementary to a part of the constant regions 2, thereby forming a hybridization stem flanking the core region (FIG. 2). In one embodiment, the part which is complementary in each constant region does not overlap with the primer binding part.

In one embodiment, the 5' end of constant region 1 of the single-stranded DNA strands in step (a) is labeled. Such labels are known to the person skilled in the art including but not limited to a fluorophore such as a cyanine, e.g., Cy3 or Cy5. Preferably the molecular size of the label is small enough that it does not interfere with the cleavage activity and/or subsequent steps of the selection method. In one embodiment, the label of the single-stranded DNA strands in step (a) is not present in the first round of the selection method. In this case, the label might be introduced with primer 1 in step (h).

The self-cleaving conditions in step (b) may vary and may dependent, e.g., on a specific cleavage reaction or the enrichment degree during the in vitro selection progression. The cleavage conditions may be adapted between different rounds of selection to modify the selection pressure. Such conditions may comprise incubation time, temperature, pH, buffers, and cofactors. In one embodiment, the self-cleaving conditions in step (b) comprise one or more ions, preferably positively charged ions. The ions may be monovalent, divalent and/or polyvalent ions. Specific examples are $Na^{+}$, $Zn^{2+}$, $Mg^{2+}$, $Mn^{2+}$, $Cu^{2+}$, or $Ca^{2+}$. In one embodiment, the ion is $Zn^{2+}$ or a combination of $Zn^{2+}$ and $Mg^{2+}$ or combination of $Zn^{2+}$, $Ca^{2+}$ and $Mg^{2+}$, preferably the ion is $Zn^{2+}$. The concentration of the ions may be in the range between about 100 nM mM to 100 mM, or about 1 mM to 50 mM, or about 5 mM to 25 mM.

In one embodiment, the self-cleaving conditions in step (b) comprise a temperature in a range of about 10-65° C., or about 15-45° C., or about 20-40° C., or about 25-35° C.

In one embodiment, the self-cleaving conditions in step (b) comprise a pH in a range of about 6.8-8.2, or about 6.8-8.0 or about 7.0 to 7.5, or about 7.1 to 7.4.

In one embodiment, the pH is in the range of about 7.1 to 7.2 and the temperature is in the range of about 21-25° C.

In one embodiment, the self-cleaving conditions in step (b) comprise a buffer. Buffers are known to the person skilled in the art and are preferably selected with regard to the specific pH or pH range during the cleavage reaction. For example, a buffer may be selected from (4-(2-hydroxyethyl)-1-piperazineethansulfonic acid) (HEPES), tris(hydroxymethyl)aminomethane (Tris), 3-(N-morpholino)propanesulfonic acid (MOPS), 2-(N-morpholino) ethanesulfonic acid (MES), piperazine-N,N'-bis(2-ethanesulfonic acid) (PIPES), Phosphate buffered saline (PBS).

In one embodiment, the self-cleaving conditions in step (b) comprise an incubation time of about 15 min. to 24 hours, or of about 30 min. to 20 hours, or of about 60 min. to 18 hours.

The incubation time may be constant during different rounds of selection. Alternatively, the incubation time may be increased or decreased between different rounds of selection. In one embodiment, the incubation time is progressively decreased in subsequent selection rounds after the first selection round. In one embodiment, the self-cleaving conditions in step (b) comprise and incubation time of 15 to 20 hours, preferably 18 hours, in the first round and an incubation time which is progressively decreased in subsequent rounds, preferably to 20 min. in round 9.

The cleavage products in step (c) may be isolated by any method known in the art, preferably by polyacrylamide gel electrophoresis (PAGE) or magnetic beads. For the purpose of the invention, isolating and, optionally tracking (in case the single-stranded DNA strands of step (a) have been labeled), in step (c) preferably comprises PAGE, e.g., urea-PAGE. As PAGE separates the molecules according to their molecular mass, PAGE may be used to implement selective pressure on the cleavage site.

In step (c), at least cleavage products 1 and cleavage products 2 are obtained. The composition of the cleavage products may vary depending on the exact cleavage site(s). Step (c) may involve the isolation of specific cleavage products to enrich single-stranded DNA strands with a use-defined cleavage site. In one embodiment, cleavage products are isolated wherein the cleavage site is between the catalytic core and the constant region 1. In this embodiment, cleavage products 2 comprise the constant region 2, the core region and a DNA self-cleaving activity and cleavage products 1 comprise the constant region 1. In another embodiment, cleavage products are isolated wherein the cleavage site is within constant region 1. In this embodiment, cleavage products 2 comprise the constant region 2, the core region, a DNA self-cleaving activity, and a part of the constant region 1 and cleavage products 1 comprise the remaining part of constant region 1.

In one embodiment, the self-cleaving activity is present is present in a catalytic core region.

In one embodiment, step (c) optionally isolating cleavages products 1 comprising the constant region 1 or the remaining part of the constant region 1.

In one embodiment, the cleavage products 1 isolated in step (c) are further analyzed to confirm the cleavage site. Methods for analyzing cleavage sites are known in the art including but not limited to DMS ladder, e.g., as described in the Example, or mass-spectrometry.

In step (d), complements of the cleavage products 2 are produced. Any method known in the art for producing complementary sequences can be used. In one embodiment, producing in step (d) comprises a linear amplification reaction, preferably wherein a primer 2 binds to the primer binding region of constant region 2. Extension of the bound primer 2 is preferably performed via a polymerase chain reaction (PCR), preferably with a hot start polymerase.

Amplification conditions are known to the skilled person and might include but not limited to 2 min at 95° C., 10×[30 s at 95° C., 30 s at 61° C., 30 s at 72° C.], 5 min at 72° C. A PCR in presence of only one primer results in linear amplification but allows for capture of minimal amounts of complements of the single-stranded DNA strands with cleavage activity.

In one embodiment, the complements produced in step (d) comprise a hydroxyl group at their 3' end. This allows for their recovery to the full-length complement regardless of the cleavage reaction by ligation of the complements comprising the constant region 1 or the complements comprising the remainder of constant region 1 in step (f).

In one embodiment, the primer 2 comprises a tag which allows to separate the complement from its template, e.g., the cleavage products 2, preferably wherein the tag is linked via a linker. In one embodiment, the tag is linked to the 5' end of the primer 2. The nature of the tag is not critical, and tags are known to the person skilled in the art including but not limited to a polyT-tail or a magnetic bead. Suitable linkers are known to the skilled person including but are not limited to a carbon-linker, preferably a C6 linker.

The primer 2 may also be labeled. In one embodiment, the label is linked to the 5' end of the primer 2. In another embodiment, the label is linked to the tag. In one embodiment, the label is a fluorescent label such a cyanine, e.g., Cy3 or Cy5, and a combination thereof. In one embodiment, the label of primer 2 is different from the label of the 5' end of the constant region 1 of the DNA strand in step (a), if present.

The method may involve separating in steps (e), (g) and (i). Separating might be necessary if subsequent steps of the method would be impaired or impossible. Separating might be performed by any method known in the art including but are not limited to PAGE or magnetic beads, preferably via PAGE. The skilled person might choose the tag for the primer 2 dependent on the separation method which is subsequently used. For example, in case PAGE is used for separating, the tag of the primer 2 might be a polyT-tail, to discriminate the size of the complements from their templates, e.g., the cleavage products 2.

Ligating in step (f) restores the full-length complements of the single-stranded DNA of step (a) which had a cleavage activity in step (b).

In one embodiment, ligating in step (f) is performed via a hydroxyl group at the 3' of the complements of the cleavage products 2 and/or via a phosphate group at the 5' end of complements of cleavage products 1.

In one embodiment, ligating in step (f) is performed enzymatically, e.g., with a ligase, such as T4 RNA ligase 1.

In step (h) DNA strands are obtained which comprise the full-length sense strand of the complements obtained in step (f) thereby restoring the single-stranded DNA strands with DNA self-cleaving activity which might be used in one or more further rounds of selection.

In step (h) the complements of the single-stranded DNA of step (a) which had a cleavage activity in step (b) are amplified. In one embodiment, amplifying comprises PCR, preferably with a hot start polymerase. In one embodiment, PCR is performed with a labeled and/or tagged primer 2 binding to the primer binding region of the constant region 2 and a primer 1 binding to the complement of the primer binding region of the constant region 1. In a preferred embodiment, the PCR is a 2-stage PCR. In the first stage, the complements of step (f) are used as a template to obtain PCR-I reaction with the primer 2 binding to the primer binding region of the constant region 2 and a primer 1 binding to the complement of the primer binding region of the constant region 1. The conditions of the first stage might be 2 min at 95° C., 10×[30 s at 95° C., 30 s at 63° C., 40 s at 72° C.], 5 min at 72° C. PCR-I reaction may be used directly as a template for the second stage which is also performed with primers 2 and primer 1. The conditions of the second stage might be 2 min at 95° C., 15×[30 s at 95° C., 30 s at 63° C., 40 s at 72° C.], 5 min at 72° C. In one embodiment, the primer 1 in step (h) is labeled to obtain DNA strands comprising the self-cleaving activity with a labeled 5' end. Preferably, the label of primer 1 is different from the label of primer 2, if present.

To increase sequence diversity, an error prone PCR (EP-PCR) step might be introduced. Preferably the EP-PCR step is introduced in round 2 or in a later round such as round 3, round 4, round 5, round 6, round 7, round 8, round 9, round 10, round 11 or round 12. In one embodiment, the EP-PCR of step (j) is performed with the DNA strands comprising the self-cleaving activity of step (h) after 9 rounds followed by about another 3 rounds without EP-PCR. In one embodiment, the EP-PCR of step (j) introduces a mutagenesis rate in a range of about 2.0-9.0%, or about 2.5-8.0% relative to the total number nucleotides present in the core region.

In one embodiment, the DNA strands comprising the self-cleaving activity are subjected to one or more steps (a)-(h) and optionally (i) and (j). In one embodiment, the DNA strands comprising the self-cleaving activity are subjected to one or more rounds until the cleavage activity results in a final yield Ymax of about 70% or more, about 80% or more, about 90% or more, about 92% or more, about 95% or more, about 96% or more, or about 97% or more, or about 98% or more, or about 99% or more. In one embodiment, the final yield Ymax is calculated by Y=Ymax(1−e−kobs*t) wherein Y is the reaction yield and t is a timepoint within 24 hours after start of the reaction, preferably after about 24 hours of the start of the reaction.

In one embodiment, the DNA strands comprising the self-cleaving activity are subjected to about 8 round, or about 9 rounds, or about 10 rounds, or about 11 rounds, or about 12 rounds or about 13 rounds, or about 14 rounds or about 15 rounds of selection, preferably about 12 rounds.

In another aspect, the invention relates to a DNAzyme obtainable by the method according to the invention, preferably wherein the DNAzyme comprises a self-cleaving activity between the catalytic core and the constant region 1 or within constant region 1.

In another aspect, the invention relates to a DNAzyme comprising the following sequence:

(SEQ ID NO: 1)

5'-$N^{\&}$ G $Y^{\$}$ $Y^{\#}$ GT $N^{\$}$ $Y^{\#}$ ACGC $Y^{\#}$ $Y^{\$}$ YGTCTTATCGGTT $Y^{\$}$ $Y^{\$}$ $N^{\#}$ N-3', wherein A is a nucleotide with the base adenine, C is a nucleotide with the base cytosine, G is a nucleotide with the base guanine, T is a nucleotide with the base thymidine, N is independently A, C, G, or T, Y is independently C or T, $ is independently preferably T, # is independently preferably C,

& is independently preferably G, and wherein the DNAzyme comprises a self-cleaving activity, optionally wherein an additional nucleotide N# is included between nucleotide position 29 and 30 of SEQ ID NO: 1, wherein the numbering of nucleotides is from 5' to 3' direction of SEQ ID NO: 1.

In another embodiment, the DNAzyme is selected from any one of the sequences given in the following table in 5' to 3' direction:

TABLE 1

| | | | |
|---|---|---|---|
| A cleavers | SEQ ID NO: 24 | RT-3-A | A\| GGTCGTTCACGCCTCGTCTTATCGGTTTTCA |
| | SEQ ID NO: 25 | RT-7-A | A\| GGTCGTTCACGCCTTGTCTTATCGGTTTTCA |
| | SEQ ID NO: 26 | RT-9-A | A\| GGTCGTTCACGCTTCGTCTTATCGGTTTTCA |
| | SEQ ID NO: 27 | RT-12-A | A\| TGTCGTTCACGCCTCGTCTTATCGGTTTTCA |
| | SEQ ID NO:28 | RT-15-A | A\| GGTCGTACACGCCTTGTCTTATCGGTTTTCA |
| | SEQ ID NO: 29 | RC-4-A | A\| GGTCGTTCACGCCTCGTCTTATCGGTTTTCG |
| | SEQ ID NO: 30 | RC-15-A | A\| GGTCGTTCACGCCTTGTCTTATCGGTTTTCG |
| T cleavers | SEQ ID NO: 31 | RT-7 | T\| GGTCGTTCACGCCTTGTCTTATCGGTTTTCA |
| | SEQ ID NO: 32 | RT-12 | T\| TGTCGTTCACGCCTCGTCTTATCGGTTTTCA |
| | SEQ ID NO: 33 | RC-5-T | T\| GGCTGTTCACGCCTTGTCTTATCGGTTTTCG |
| C cleavers | SEQ ID NO: 34 | RT-7-C | C\| GGTCGTTCACGCCTTGTCTTATCGGTTTTCA |
| | SEQ ID NO: 35 | RT-12-C | C\| TGTCGTTCACGCCTCGTCTTATCGGTTTTCA |
| | SEQ ID NO: 36 | RC-5 | C\| GGCTGTTCACGCCTTGTCTTATCGGTTTTCG |
| | SEQ ID NO: 37 | RC-15 | C\| GGTCGTTCACGCCTTGTCTTATCGGTTTTCG |
| G cleavers | SEQ ID NO: 38 | RT-3-G | G\| GGTCGTTCACGCCTCGTCTTATCGGTTTTCA |
| | SEQ ID NO: 39 | RT-7-G | G\| GGTCGTTCACGCCTTGTCTTATCGGTTTTCA |
| | SEQ ID NO: 40 | RT-9-G | G\| GGTCGTTCACGCTTCGTCTTATCGGTTTTCA |
| | SEQ ID NO: 41 | RT-15-G | G\| GGTCGTACACGCCTTGTCTTATCGGTTTTCA |
| | SEQ ID NO: 42 | RC-15-G | G\| GGTCGTTCACGCCTTGTCTTATCGGTTTTCG |
| | SEQ ID NO: 43 | RG-3 | G\| GGTCGTTCACGCCTTGTCTTATCGGTTCCTCC |
| | SEQ ID NO: 44 | RG-5 | G GGTCGTTCACGCCTCGTCTTATCGGTTTTCC |
| | SEQ ID NO: 45 | RG-8 | G\| GGTCGTTCACGCCTCGTCTTATCGGTTCCTCC |
| | SEQ ID NO: 46 | RG-11 | G\| GGTCGTTCACGCCTTGTCTTATCGGTTTTCC |
| | SEQ ID NO: 47 | 12-11 parent | GGTCGTGTACGCCTCGTCTTATCGGTTATCT |

Thus, in a further aspect, the DNAzyme comprises the following sequence:

(SEQ ID NO: 2)

5'-N$^{\&}$ G Y$^{\$}$ Y$^{\#}$ GT N$^{\$}$ Y$^{\#}$ ACGC Y$^{\#}$ Y$^{\$}$ YGTCTTATCGGTT Y$^{\$}$ N$^{\#}$ Y$^{\$}$ N$^{\#}$ N-3', wherein A is a nucleotide with the base adenine, C is a nucleotide with the base cytosine, G is a nucleotide with the base guanine, T is a nucleotide with the base thymidine, N is independently A, C, G, or T, Y is independently C or T, $ is independently preferably T, # is independently preferably C,

& is independently preferably G, and wherein the DNAzyme comprises a self-cleaving activity.

In another embodiment, the DNAzyme is an A-cleaver, i.e., it cleaves after a nucleotide A, e.g., after the final nucleotide A of the 5' constant region of the single stranded DNA strand such as DNAzymes with a sequence selected from SEQ ID NOs: 24-30 preferably SEQ ID NOs: 24-30 or 47.

In another embodiment, the DNAzyme is a T-cleaver, i.e., it cleaves after a nucleotide T, e.g., after the final nucleotide T of the 5' constant region of the single stranded DNA strand such as DNAzymes with a sequence selected from SEQ ID NOs: 31-33.

In another embodiment, the DNAzyme is a C-cleaver, i.e., it cleaves after a nucleotide C, e.g., after the final nucleotide C of the 5' constant region of the single stranded DNA strand such as DNAzymes with a sequence selected from SEQ ID NOs: 34-37.

In another embodiment, the DNAzyme is a 0-cleaver, i.e., it cleaves after a nucleotide 0, e.g., after the final nucleotide 0 of the 5' constant region of the single stranded DNA strand such as DNAzymes with a sequence selected from SEQ ID NOs: 38-46, preferably SEQ ID NOs: 38-47.

In one embodiment, the self-cleaving activity results in a final yield $Y_{max}$ of about 60% or more, about 70% or more, about 80% or more, about 90% or more, about 92% or more, about 95% or more, about 96% or more, or about 97% or more, or about 98% or more, or about 99% or more, preferably wherein the final yield $Y_{max}$ is calculated by Y=Ymax(1−e−kobs*t) wherein Y is the reaction yield and t is a timepoint within 24 hours after start of the reaction, preferably after about 24 hours of the start of the reaction.

In one embodiment, the DNAzyme has a $k_{obs}$ in a range of 0.005 $min^{-1}$ to 0.240 $min^{-1}$, or of 0.35 $min^{-1}$ to 0.140 $min^{-1}$, or of 0.050 $min^{-1}$ to 0.100 $min^{-1}$, preferably wherein $k_{obs}$ is calculated by: $Y=Y_{max}(1-e^{-kobs*t})$ wherein Y is the reaction yield and t is a timepoint within 24 hours after start of the reaction, preferably after about 24 hours of the start of the reaction.

In one embodiment, the final yield $Y_{max}$ is determined from a DNAzyme reaction in the presence of $Zn^{2+}$, at about 25-40° C. and/or a pH of about 6.8-7.3. More preferably, the final yield is determined from a DNAzyme reaction in the presence of $Zn^{2+}$, at a pH of 6.8-7.1 and/or a temperature of 35° C.

In one embodiment, the self-cleaving activity is a hydrolytic cleavage activity, e.g., it results in a hydroxyl group at the 3' end and a phosphate group at the 5' end.

In a further aspect, the invention relates to the use of a DNAzyme of the invention in the production of single stranded DNA molecules.

In one embodiment, said use comprises:

(a) providing a pseudogene nucleic acid, wherein said pseudogene nucleic acid is a nucleic acid that comprises at least one target DNA oligo- or polynucleotide sequence and two self-cleaving DNA sequences flanking each target DNA oligo- or polynucleotide sequence,
(b) integrating the pseudogene nucleic acid into a vector, transforming bacterial cells with said vector and producing a precursor ssDNA from said vector under bacterial culture conditions, wherein said precursor ssDNA comprises the pseudogene nucleic acid;
(c) isolating the precursor ssDNA from the bacterial culture;
(d) digesting the precursor ssDNA under reaction conditions where the self-cleaving DNA sequences become active; and
(e) separating the target single stranded DNA oligo- or polynucleotide(s) and obtaining the target single stranded DNA oligo- or polynucleotide(s)
  wherein at least one of the two self-cleaving DNA sequences are DNAzymes of the present invention, such as a DNAzyme of any one of SEQ ID NO: 1, 2, or 24-47, optionally 24-46.

In one embodiment, the two DNAzymes of the present invention are the same or different. In one embodiment, one of the two self-cleaving DNA sequences is a DNAzyme of the present invention, such as a DNAzyme of any one of SEQ ID NO: 1, 2, 24-47, optionally 24-46 and the other is another DNAzyme with self-cleaving activity. The self-cleaving activity of the other DNAzyme is preferably activated by the same conditions as the self-cleaving activity of the DNAzymes of the present invention, preferably by the same monovalent or divalent ions as the DNAzyme of the present invention, more preferably by $Zn^2$. In a specific embodiment, the other DNAzyme is selected from I-R3 or variants thereof such as described in Gu et al., 2013; II-R1 or variants thereof such as described in Qiao Zhang et al., 2022; II-R2 or variants thereof such as described in Qiao Zhang et al., 2022; II-R3 or variants thereof such as described in Qiao Zhang et al., 2022; 13PD1 or variants thereof such as described in Qiao Zhang et al., 2022; and combinations thereof.

For example, for production of ssDNA, a phagemid is comprised of user defined sequences interleaved with self-cleaving DNA sequences (DNAzymes). After the ssDNA is produced in phage culture at scale, the target ssDNA strands can be digested, separated, and readily used for assembly of DNA origami (or in other applications that employ ssDNA, such as homology directed repair for CRISPR/CAS gene editing).

The single stranded DNA molecules can be used in DNA nanotechnology, e.g., they can be assembled and/or folded into DNA origami structures, (tile-based) DNA nanostructures, or crystalline DNA nanomaterials as described in the prior art, e.g., in WO 2018/054571, particularly pages 10-14 and the Examples.

Such nanostructures may be used in medicine or therapy. For example, DNA-based nanostructures can be used for encapsulating a virus, viral particle. Such nanostructures are described in the prior art, e.g., in WO 2021/165528.

As a further example, DNA-based nanostructures can be used in gene therapy. For example, the ssDNA molecules can be used to build nucleic acid nanostructures comprising at least one scaffold strand and a plurality of staple strands, wherein said nanostructure, preferably said at least one scaffold strand, comprises at least one nucleic acid sequence encoding a gene wherein preferably the gene is a gene involved in a pathological pathway, a gene suitable for a vaccination, a gene for genome editing, and/or a CRISPR-based gene. In one embodiment, the gene is selected from prokaryotic genes, viral genes, and eukaryotic genes. In one embodiment, the gene is selected from prokaryotic genes such as CRISPR-based genes and eukaryotic genes such as human genes. In a preferred embodiment, the gene is a eukaryotic gene, preferably a mammalian gene, e.g., a human gene. Such nucleic acid nanostructures are known in the art, e.g., from EP22207474. Alternatively, the ssDNA molecules can be used as aptamers for other molecules or can bind or process other molecules wherein preferably the molecule is a molecule involved in a pathological pathway.

The single stranded DNA molecules can be further used in diagnosis. For example, the ssDNA molecules can bind, detect, or process other molecules, wherein preferably the molecule is a molecule involved in a pathological pathway. The ssDNA may also be used to bind, detect, or process other molecules in research.

The ssDNA may also be used as a probe for sequencing or DNA synthesis such as polymerase chain reactions. Such methods are known by the person skilled in the art and comprise classic sequencing methods such as Maxam and Gilbert sequencing and Sanger sequencing and next-generation sequencing methods such as Illumina sequencing, and pyrosequencing.

The ssDNA may also be used in genome editing. For example, the ssDNA molecules can be used in CRISPR/Cas-based genomic editing, e.g., for homology directed repair (HDR).

Such methods are known to the person skilled in the art, e.g., from Bai et al., 2020 or Quadros et aL, 2017. For examples, HRD might be used to introduce mutations or in gene therapy methods to replace and correct mutated genetic information in a subject.

In one aspect, the invention provides a method for the recombinant production of ssDNA molecules, comprising the steps of (a) providing a pseudogene nucleic acid,
 wherein said pseudogene nucleic acid is a nucleic acid that comprises at least one target DNA oligo- or polynucleotide sequence and two self-cleaving DNA sequences flanking each target DNA oligo- or polynucleotide sequence,
(b) integrating the pseudogene nucleic acid into a vector, transforming bacterial cells with said vector and producing a precursor ssDNA from said vector under bacterial culture conditions, wherein said precursor ssDNA comprises the pseudogene nucleic acid;
(c) isolating the precursor ssDNA from the bacterial culture;
(d) digesting the precursor ssDNA under reaction conditions where the self-cleaving DNA sequences become active; and
(e) separating the target single stranded DNA oligo- or polynucleotide(s) and obtaining the target single stranded DNA oligo- or polynucleotide(s)
 wherein at least one of the two self-cleaving DNA sequences are DNAzymes of the present invention, such as a DNAzyme of any one of SEQ ID NO: 1, 2, 24-47, optionally 24-46.

In one embodiment, the two DNAzymes of the present invention are the same or different. In one embodiment, one of the two self-cleaving DNA sequences is a DNAzyme of the present invention, such as a DNAzyme of any one of SEQ ID NO: 1, 2, 24-47, optionally 24-46 and the other is another DNAzyme with self-cleaving activity. The self-cleaving activity of the other DNAzyme is preferably activated by the same conditions as the self-cleaving activity of the DNAzymes of the present invention, preferably by the same monovalent or divalent ions as the DNAzyme of the present invention, more preferably by $Zn^{2+}$. In a specific embodiment, the other DNAzyme is selected from I-R3 or variants thereof such as described in Gu et al., 2013; II-R1 or variants thereof such as described in Qiao Zhang et al., 2022; II-R2 or variants thereof such as described in Qiao Zhang et al., 2022; II-R3 or variants thereof such as described in Qiao Zhang et al., 2022; 13PD1 or variants thereof such as described in Qiao Zhang et al., 2022; and combinations thereof.

The present invention is further characterized by the following embodiments:

1. Method for selecting a DNAzyme with self-cleaving activity, the method comprising:
 (a) providing a plurality of single-stranded DNA strands,
  wherein each single-stranded DNA strand comprises a core region of random nucleotides flanked by a constant region 1 at its 5' end and a constant region 2 at its 3' end, and
  wherein each constant region comprises a primer binding part;
 (b) subjecting the plurality of single-stranded DNA strands to self-cleaving conditions;
 (c) isolating cleavage products 2, and optionally isolating cleavage products 1,
  wherein the cleavage products 2 comprise the constant region 2, the core region, and
  wherein the cleavage products 2 comprise a DNA self-cleaving activity, and
  wherein the cleavage products 1 comprise the constant region 1,
  preferably wherein cleavage of the single-stranded DNA strands occurred between the catalytic core and the constant region 1,
  or
  wherein the cleavage products 2 comprise the constant region 2, the core region, and a part of constant region 1, and
  wherein the cleavage products 2 comprise a DNA self-cleaving activity, and
  wherein the cleavage products 1 comprises the remaining part of the constant region 1,
  preferably wherein cleavage of the single-stranded DNA strands occurred within the constant region 1;
 (d) producing complements of the cleavage products 2;
 (e) optionally separating the complements of the cleavage products 2;
 (f) ligating the 3' end of the complements of the cleavage products 2 to complements of the cleavage products 1, thereby obtaining complements of single-stranded DNA strands of step (a) with the DNA self-cleaving activity;
 (g) optionally separating the complements of the single-stranded DNA strands;
 (h) amplifying the complements of the single-stranded DNA strands thereby obtaining DNA strands comprising the DNA self-cleaving activity;
 (i) optionally separating the DNA strands comprising the self-cleaving activity;
 (j) optionally subjecting the DNA strands comprising the self-cleaving activity to an error prone (EP-PCR) step; and
 (k) optionally subjecting the DNA strands comprising the self-cleaving activity of step
 (h), optionally of steps (i) or j), to one or more rounds of steps (b)-(h), and optionally to one or more rounds of steps (i) and/or (j).

2. The method of embodiment 1, wherein the constant regions 1 of the single-stranded DNA strands in step (a) comprise a part which is complementary to a part of the constant regions 2, thereby forming a hybridization stem flanking the core region.

3. The method of embodiment 1 or 2, wherein the core region of the single-stranded DNA strands in step (a) comprises about 14-100 nucleotides, or about 20-100 nucleotides, or about 25-50 nucleotides, or about 30-40 nucleotides, or about 32-35 nucleotides.

4. The method of any one of the preceding embodiments, wherein the 5' end of constant region 1 of the DNA strand in step (a) is labeled.

5. The method of any one of the preceding embodiments, wherein the self-cleaving conditions in step (b) comprise one or more ions, preferably monovalent, divalent and/or trivalent and/or polyvalent ions, such as $Na^{+}$, $Zn^{2+}$, $Cu^{2+}$, $Mn^{2+}$, $Mg^{2+}$, $Ca^{2+}$, and/or PLL-g-Dex.

6. The method of any one of the preceding embodiments, wherein the self-cleaving conditions in step (b) comprise a temperature in a range of about 10-62° C., or about 15-45° C., or about 20-40° C., or about 25-35° C.

7. The method of any one of the preceding embodiments, wherein the self-cleaving conditions in step (b) comprise a pH in a range of about 6.8-8.2, or about 6.8-8.0 or about 7.0 to 7.5.

8. The method of any one of the preceding embodiments, wherein the self-cleaving conditions in step (b) comprise a buffer, such as (4-(2-hydroxyethyl)-1-piperazineethansulfonic acid) (HEPES).

9. The method of any one of the preceding embodiments, wherein the self-cleaving conditions in step (b) comprise an incubation time of about 30 minutes to 20 hours, preferably of about 1 to 20 hours, preferably of about 2 to 20 hours, preferably of about 3 to 20 hours, preferably of about 5 to 20 hours, preferably of about 10 to 20 hours, preferably of about 15 to 20 hours in the first round, preferably about 18 hours.

10. The method of any one of the preceding embodiments, wherein the self-cleaving conditions in step (b) comprise an incubation time of about 30 minutes to 20 hours, preferably of about 15 to 20, preferably about 18, hours in the first round and an incubation time which is progressively decreased in subsequent rounds.

11. The method of any one of the preceding embodiments, wherein isolating in step (c) comprises polyacrylamide gel electrophoresis (PAGE).

12. The method of any one of the preceding embodiments, wherein in step (c) the cleavage products 2 comprise the core region, the constant region 2 and a self-cleaving activity, and wherein the cleavage products 1 comprise the constant region 1, and wherein cleavage of the single-stranded DNA strands occurred between the catalytic core and the constant region 1.

13. The method of any one of the preceding embodiments, wherein the cleavage products 1 isolated in step (c) are further analyzed to confirm the cleavage site.

14. The method of any of the preceding embodiments, wherein producing in step (d) comprises a linear PCR amplification.

15. The method of any of the preceding embodiments, wherein producing in step (d) comprises a linear PCR amplification with a primer 2 binding to the primer binding region of constant region 2.

16. The method of embodiment 15, wherein the primer 2 comprises a tag, preferably a tag which is linked to the 5' end of the primer 2.

17. The method of embodiment 16, wherein the tag is selected from the group consisting of a polyT-tail and a magnetic bead, preferably wherein the tag is linked to the primer 2 via a linker.

18. The method of any of the preceding embodiments, wherein separating in steps (e), (g) and (i) is performed via PAGE or via magnetic beads, preferably via PAGE.

19. The method of any of the preceding embodiments, wherein ligating in step (f) is performed via a hydroxyl group at the 3' of the complements of the cleavage products 2.

20. The method of any of the preceding embodiments, wherein ligating in step (f) is performed via a phosphate group at the 5' end of complements of cleavage products 1.

21. The method of any of the preceding embodiments, wherein ligating in step (f) is performed enzymatically.

22. The method of any of the preceding embodiments, wherein amplifying in step (h) comprises a polymerase chain reaction (PCR).

23. The method of any of the preceding embodiments, wherein amplifying in step (h) comprises a 2-stage PCR.

24. The method of any of the preceding embodiments, wherein amplifying in step (h) comprises a polymerase chain reaction (PCR) with a primer 2 binding to the primer binding region of constant region 2 and a primer 1 binding to the complement of the primer binding region of constant region 1.

25. The method of embodiment 24, wherein the primer 2 in step (h) is tagged and/or the primer 1 in step (h) is labeled to obtain DNA strands comprising the self-cleaving activity with a labeled 5' end.

26. The method of any of the preceding embodiments, wherein the EP-PCR of step 0) is performed with the DNA strands comprising the self-cleaving activity of step (h) after 9 rounds followed by about another 3 rounds without EP-PCR.

27. The method of any of the preceding embodiments, wherein the EP-PCR of step (j) aims at a mutagenesis rate in a range of about 2.0-9.0%, or about 2.5-8.0% relative to the total number nucleotides present in the core region.

28. A DNAzyme obtainable by the method according to any one of embodiments 1 to 27, preferably wherein the DNAzyme comprises a self-cleaving activity between the catalytic core and the constant region 1 or within constant region 1.

29. A DNAzyme comprising a sequence selected from:

5'-$N^{\&}$ G $Y^{\$}$ $Y^{\#}$ GT $N^{\$}$ $Y^{\#}$ ACGC $Y^{\#}$ $Y^{\$}$ YGTCT-TATCGGTT $Y^{\$}$ $Y^{\$}$ $N^{\#}$ N-3' (SEQ ID NO: 1), optionally wherein an additional nucleotide $N^{\#}$ is included between nucleotide position 29 and 30 of SEQ ID NO: 1, wherein the numbering of nucleotides is from 5' to 3' direction of SEQ ID NO: 1; or (SEQ ID NO: 2)
5'-$N^{\&}$ G $Y^{\$}$ $Y^{\#}$ GT $N^{\$}$ $Y^{\#}$ ACGC $Y^{\#}$ $Y^{\$}$ YGTCTTATCGGTT
$Y^{\$}$ $N^{\#}$ $Y^{\$}$ $N^{\#}$ N-3', wherein
A is a nucleotide with the base adenine,
C is a nucleotide with the base cytosine,
G is a nucleotide with the base guanine,
T is a nucleotide with the base thymidine,
N is independently A, C, G, or T,
Y is independently C or T,
S is independently G or C,
W is independently A or T,
$ is independently preferably T,
# is independently preferably C,
& is independently preferably G, and
wherein the DNAzyme comprises a self-cleaving activity.

30. The DNAzyme of embodiments 28 or 29 wherein the DNAzyme has a sequence selected from SEQ ID NO: 24-47, optionally SEQ ID NOs: 24-46.

31. The DNAzyme of any one of embodiments 28-30, wherein the DNAzyme has a $k_{obs}$ in a range of 0.005 $min^{-1}$ to 0.240 $min^{-1}$, or of 0.35 $min^{-1}$ to 0.140 $min^{-1}$, or of 0.050 $min^{-1}$ to 0.100 $min^{-1}$, preferably wherein $k_{obs}$ is calculated by: $Y=Y_{max}(1-e^{-kobs*t})$ wherein Y is the reaction yield and t is a timepoint within 24 hours after start of the reaction, preferably after about 24 hours of the start of the reaction.

32. The DNAzyme of any one of embodiments 28-31, wherein the self-cleaving activity results in a final yield $Y_{max}$ of about 92%, about 95%, about 96%, or about 98%, wherein the final yield $Y_{max}$ is calculated by $Y=Y_{max}(1-e^{-kobs*t})$ wherein Y is the reaction yield and t is a timepoint within 24 hours after start of the reaction, preferably after about 24 hours of the start of the reaction.

33. The DNAzyme of any of embodiments 28-32, wherein the self-cleaving activity is a hydrolytic cleavage.

34. Use of the DNAzyme of any of embodiments 28-33 in the production of single stranded DNA molecules.

35. The use of embodiment 34, wherein the single stranded DNAzyme is used in DNA nanotechnology.

36. The use of embodiment 34, wherein the single stranded DNAzyme is used in genome editing.

37. The use of embodiment 36, wherein the genome editing is homology directed repair (HOR).

Example 1

Method of In Vitro Selection for Self-Cleaving DNAzyme

Our initial DNAzyme library sequence was constructed in a rather conventional fashion—the randomized core region was flanked by two constant sequences (FIG. 2). However, the later were partially complementary to each other forming terminal hybridization stem for the core loop and thus mimicking the DNAzyme cassette set up. The unhybridized parts served as primer binding regions for amplification steps. The initial library consisted of four sub-libraries. Each of them featured one of four possible base pairs at the preselected cleavage site with the intent to avoid bias towards one fixated nucleotide at the start of selection. The length of core region as short as $N_{20}$ is known to be sufficient to evolve DNA cleaving deoxyribozymes (Velez et al., 2012). Aiming to produce a DNAzyme more compact than already available I-R3 and II-R2/3, the core region was settled with $N_{32}$. High resolution urea-PAGE was used to separate, isolate and track products after each step. Additionally, the selective pressure on the cleavage site was implemented with PAGE. The isolated DNA after cleavage served as a template for primer extension via the 3' constant sequence. A cyclic PCR protocol in presence of only one primer results in linear amplification for successful capture of minimal amounts of active DNAzyme species and provided the product with 5' Cy5 label. The reaction yield indirectly indicated the library cleavage efficiency in the current round. Thus, it was used to follow the enrichment progress through selection and to adjust the incubation time for the cleavage reaction. Most importantly, the generated after primer extension DNA strand was always terminated with 3'-hydroxyl group regardless of DNAzymes original mode of action. This was readily used to perform recovery of the full library structure by adaptor ligation. For the reaction, an oligonucleotide comprised of the reverse complement of the 5' constant sequence and T4 RNA Ligase 1 were used. Subsequently, the full-sized ssDNA pool for the next round was produced using a two-step PCR amplification. The selection procedure was repeated until the library became sufficiently enriched.

Results

Identification of New Self-Cleaving Deoxyribozymes

The first noticeable activity of the DNAzyme pool was detected at round 5. To apply selective pressure towards highly active species, we progressively decreased incubation time for cleavage step from 18 hours down to 20 minutes at round 9. The primer extension reaction yield plateaued at this stage and the conducted activity assay for the corresponding DNA pools was consistent with this observation. To increase sequence diversity, we introduced an error prone PCR (EP-PCR) step after round 9 and continued selection for another 3 rounds.

The libraries of both $8^{th}$ and $12^{th}$ rounds were cloned and 76 identified unique sequences were screened for activity. The members of 4 major families exhibited activity (41 out of 76 tested sequences). Based on initial testing for each of these four families, one most prominent candidate of was chosen for further testing: 12-35, 8-35, 12-11 and 12-8. Sequence analysis revealed that directed evolution didn't dramatically affect populations of some families between round 8 and 12, including the 12-8 family. At the same time, the pool occupation by the 8-35 family dwindled under selective pressure. Most likely this happened due to competition with the 12-11 family emerging after EP-PCR. Represented by one identified inactive sequence, 8-19, at round 8, the 12-11 family evolved to dominate at round 12.

RNAse T1 digestion and alkaline hydrolysis ladders were previously used to identify the reaction sites of RNA-cleaving DNAzymes. We adapted DMS profiling method to generate analogous characteristic digestion DNA ladders and confirm the cleavage sites of the tested DNAzymes. All four catalysts performed cleavage at the very beginning of the core region, as designed. The products of reactions were also analyzed with mass-spectrometry. DNAzyme 12-11 followed hydrolytic pathway cleaving linkage between nucleotide G1 and G2 of the core region and produced distinct 3'-hydroxyl and 5'-phosphate terminated products. At the same time, 12-35, 8-35 and 12-8 demonstrated a variety of oxidative mechanisms that resulted in nucleoside excisions, despite the buffer condition in selection reaction rather favored hydrolytic cleavage. A nucleoside excision was already reported for guanosine in presence of redox-inactive Zn ions (Lee et al., 2017). Similarly, 12-35 self-cleavage resulted in removal of guanosine G1, whereas 8-35 excised cytosine C1 and 12-8 excised cytosine C1 or adjacent adenosine A2. These findings confirm the ability of our in vitro selection method to evolve DNAzymes with various action modes.

Characterization of the New Self-Cleaving Deoxyribozyme 12-11

Initial testing of 12-11 revealed high sensitivity of the DNAzyme to the pH of the cleavage buffer. The pH optimum at 25° C. spanned from 7.1 to 7.2. Moreover, thorough activity screening at different incubation temperatures revealed a "slope-like" activity profile: the activity optimum was shifting from 7.4 at 10° C. towards 6.8 at 50° C., the highest yield could be achieved in the range of 25-40° C. (>90%). Three other DNAzymes also exhibited own pH-T dependence patterns and maximum yield conditions, although the objectively low final (<60%) yield was making them unsuitable for our applications.

Incubation in presence of different bi- and monovalent ions revealed $Zn^{2+}$ dependence of 12-11. Magnesium and calcium played a modulating role, both rate and yield of self-cleavage were enhanced in the presence of these ions. However, $Ca^{2+}$ can be removed without significant loss as long as $Mg^{2+}$ is present. The reaction rate was maximized at around 3 mM and 10 mM for zinc and magnesium, respectively, when calcium was excluded. We also screened the activity of 12-11 at various concentrations of $Na^{+}$ and HEPES. Change in concentration of HEPES didn't have as much effect as elevated $Na^{+}$ concentration which led to significant decrease of reaction yield. Reducing the concentration of sodium to 50 mM universally slightly improved the yield relatively to the standard reaction.

DNAzyme 12-11 demonstrated robustness remaining active in various buffer systems, albeit pH-T activity profile had to be established for each buffer. A correlation between DNAzymes activity profile and the dpKa/dT value of buffer systems was observed. The findings suggest that 12-11 has certain innate optimal pH-T profile and in the final reaction the pH is more important than the chemical nature of a buffer system expanding compatibility of 12-11 with systems that use buffers other than HEPES.

Enhancement of 12-11 Deoxyribozyme Through Reselection

Identified in an initial in vitro selection procedure, DNAzyme 12-11 possessed the intended cleavage site and had decent yield, albeit over prolonged incubation time. Still, the catalyst was sensitive to the upstream nucleotide identity at the reaction site imposing sequence restrictions to the produced ssDNA. Aiming to achieve full generality for the DNAzyme cleavage site, a secondary in vitro selection using the sequence of 12-11 dopped to 70% was performed. Obtaining mutants with a higher reaction rate and a higher final yield in particular was another goal to be fulfilled with this reselection.

Firstly, following the same protocol as for initial selection, the library was pre-enriched until the DNA pool distinctly exhibited activity (Round R4). Then, an EP-PCR step with low mutation rate was introduced and it was proceeded by splitting the selection in four separate directed evolution experiments RA, RT, RC, and RG. Each of them featured a ligation adapter terminated with one of four nucleotides allowing to apply selective pressure to the specific nucleotide at the cleavage site from next round onwards. Upon selection completion, activity assays were performed to assess fractions of active species for DNA pools of rounds R4 to R10. All four libraries showed high enrichment degree at different stages of selection with assessed cleavage fraction surpassing 50%. The activity peak followed by the decline through selection most likely connected with eventual accumulation of parasitic sequences that prone to outcompete DNAzymes sequences in PCR amplification steps. DNA pools RA6, RT9, RC9 and RG10 were analyzed by HTS. Top 15 most frequent sequences from each library identified with HTS were screened for activity and the candidate list was restricted to 16 sequences combined with highest cleavage yield.

Methods

In Vitro Selection

The first round of selection was initiated with 500 pmol of the initial library which consisted of four equimolar sublibraries SL1-SL4. The subsequent rounds were started using 5-10 pmol of ssDNA recovered after PCR amplification step. Starting with round 2 the enriched ssDNA pools were also terminally labeled with Cy5 fluorescent dye via labeled primer in PCR amplification step. The cleavage reaction was performed at 25° C. in Cleavage buffer I containing 50 mM HEPES (pH 7.5 at 25° C.), 100 mM NaCl, 10 mM $MgCl_2$, 2 mM $ZnCl_2$, 2 mM $CaCl_2$). Duration of cleavage reaction in the first round was 18 hours and was adjusted in following rounds to increase selective pressure. The cleaved fraction was separated with 10% Urea-PAGE, weight marker WM1 was used to assist with localization of active DNA fraction in gel. Excised gel was crushed, DNA was extracted by incubation with 1× TEN buffer (10 mM Tris, 1 mM EDTA, 300 mM NaCl), recovered by precipitation with ethanol and stored as a dry pellet.

Obtained DNA was used as a template for 20 uL single primer aPCR linear amplification reaction performed with the polyT-tailed primer P1 (2 min at 95° C., 10×[30 s at 95° C., 30 s at 61° C., 30 s at 72° C.], 5 min at 72° C.). The primer P1 was also terminally labeled with Cy5 allowing to track the reaction products in PAGE gel. The reverse complement product of active DNAzyme pool was isolated by Urea-PAGE assisted by weight marker WM2 as described above.

The ligation reaction was performed to restore the cleaved off constant sequence. The reaction was performed on 20 uL scale and was conducted by T4 RNA Ligase 1 (New England Biolabs) using 75 pmol of adaptor LA1 following the manufacturer's instructions. Ligated DNA was isolated by Urea-PAGE using the Cy5 label carried over from the previous step and assisted by weight marker WM3 as described above.

The PCR amplification of enriched DNA pool was performed in two stages. In the first stage the isolated ligation product was used as template for 20 uL PCR-I performed with primers P1 and P2 (2 min at 95° C., 10×[30 s at 95° C., 30 s at 63° C., 40 s at 72° C.], 5 min at 72° C.). Upon completion, 2.5 uL of PCR-I reaction were used directly as a template of 20 uL PCR-II also performed with primers P1 and P2 (2 min at 95° C., 15×[30 s at 95° C., 30 s at 63° C., 40 s at 72° C.], 5 min at 72° C.). The amplification reactions (as well as mentioned above single primer aPCR) were performed by Phusion Hot Start Flex Polymerase (New England Biolabs) with 5× Phusion GC Buffer following manufacturer's instructions. Remaining PCR-1 reaction was diluted to 100 uL with 1× TEN Buffer and purified using phenol-chloroform extraction followed by precipitation with ethanol. The dry pellet was stored at −20° C. and served as a back-up of the current selection round. The amplified sense ssDNA DNAzymes pool was isolated from PCR 11 reaction by Urea-PAGE assisted by weight marker WM4 as described above. The polymerase might occasionally make errors resulting in insertions and deletions of nucleotides resulting a certain variability at the 3' end of the core region of one or more nucleotides, i.e., a shorter or longer DNAzyme sequence compared to sequence of the initial core region without affecting the cleavage efficacy.

The error-prone PCR (EP-PCR) was used to increase sequence diversity at certain rounds of selection. EP-PCR was performed on the scale of 50 uL using JBS dNTP-Mutagenesis Kit (Jena Bioscience) following the manufacturer's instruction. The reaction used 2.5 uL of PCR I reaction as a template, the reaction was conducted for 15 (after round 9) or 5 (after round 3) cycles aiming for 8.0% or 2.5% of mutagenesis rate, respectively. To remove mutagenic dNTP analogs, EP-PCR reaction mixture was purified using QIAquick PCR Purification Kit (Qiagen). Obtained DNA then was converted to natural nucleotide composition with PCR 11 reaction performed for only 5 cycles.

Reselection

The reselection of 12-11 DNAzyme was conducted in the same fashion as the initial selection with a few changes. The initial pool sequence was based on 12-11 DNAzyme identified in the initial selection. The first round of selection was initiated with 400 pmol of degenerate library containing 12-11 catalytic core sequence doped to 70%. The cleavage reaction was performed at 25° C. in Cleavage buffer II containing 50 mM HEPES (pH 7.0 at 25° C.), 50 mM NaCl, 10 mM $MgCl_2$, 2 mM $ZnCl_2$, 2 mM $CaCl_2$. The ligation reaction was performed with adaptor LA1 for the first 3 rounds. At the round 4 the reselection procedure was split out in four separate ones. The PAGE purified product of aPCR was split equally and ligated in four separate ligation reaction with adaptors LA2-LA5 starting from here till the end of selection (we pre-enriched).

The consensus sequences were built manually by taking into consideration the parent sequence 12-11 and the tested DNAzyme sequences with top cleavage activity (final yield at least 90%) by considering 1000 hits on average in selection pools.

DMS Ladder for Identification of Cleavage Site

The DNAzyme oligonucleotides double labeled with terminal Cy3 and Cy5 dyes (50 pmol) were dissolved in 20 μL of 1× TE Buffer. The oxidation was initiated by addition of 4 uL of fresh 10% dimethyl sulphate (DMS) in water. The reaction mixture was incubated at 25° C. for 6 minutes and then terminated by 125 uL of stop solution (200 mM 2-mercaptoethanol, 300 mM NaCl). To completely quench and remove DMS, the solution was incubated for 10 minutes at 37° C. followed with precipitation by ethanol. The dry pellet was dissolved in 50 uL of fresh 10% piperidine in water and incubated at 95° C. for 25 minutes to cleave oxidized DNA. Solution was evaporated under vacuum. To remove traces of piperidine, DNA pellet was redissolved in 50 uL of water and solution was evaporated, this step was repeated once more. Obtained DMS-ladder was separated with high resolution Urea-PAGE next to the corresponding cleavage reaction to identify the location of the cleavage site.

The DNAzyme oligonucleotides double labeled with terminal Cy3 and Cy5 dyes (50 umol) were dissolved in 20 uL of 1× TE Buffer. The oxidation was initiated by addition of 4 uL of fresh 10% dimethyl sulphate (DMS). The reaction mixture was incubated at 25° C. for 6 minutes and then terminated by 125 uL of stop solution (200 mM 2-mercaptoethanol, 300 mM NaCl). To completely quench and remove DMS, the solution was incubated for 10 minutes at 37° C. followed with precipitation by ethanol. The dry pellet was dissolved in 50 uL of fresh 10% piperidine and incubated at 95° C. for 25 minutes to cleave oxidized DNA. Solution was evaporated under vacuum. To remove traces of piperidine, DNA pellet was redissolved in 50 uL of water and solution was evaporated, this step was repeated once more. Obtained DMS-ladder was separated with high resolution Urea-PAGE next to the corresponding cleavage reaction to identify the location of the cleavage site.

Kinetic Analysis of DNAzyme Self-Cleavage Activity

Reaction mixture was prepared with 5× Cleavage buffer (1× concentration: 50 mM HEPES [pH 7.00 at 25° C.], 25 mM NaCl, 10 mM $MgCl_2$) and 5 pmol of DNAzyme. The reaction was initiated by addition of $ZnCl_2$ to required final concentration and the final reaction volume of 10 μL, immediately preceding to incubation at 35° C. The 1 uL aliquots were taken over the course of the reaction at designed timepoints and immediately quenched with 3 uL of Stop solution (80% formamide, 1×TBE, 50 mM EDTA). Obtained samples were resolved with 12% Urea-PAGE and the gel was imaged with Typhoon FLA 9500 laser scanner. Cleavage yields were quantified with densitometry by Image Lab Software. The $k_{obs}$ value was obtained by fitting the yield-versus-time data directly to first-order kinetics $Y=Y_{max}(1-e^{kobs*t})$, where Y—yield at current time point, $Y_{max}$—final yield, $k_{obs}$—observed rate of the reaction, t—time. The final yield was preferably determined by assessing the yield after prolonged incubation time, preferably 24 hours.

In order to quantify the yield of cleavage, the cleaved and uncleaved DNA molecules were separated with PAGE since these two species differ in electrophoretic mobility due to different size. The detection was performed with DNAzyme molecules that were end-labeled with a detectable fluorophore molecule.

Quantification was performed by producing an image of the gel with a laser-scanner (TyphoonFLA9000), with subsequent densitometric determination of pixel values of obtained DNA bands using software (ImageLab-BioRad). This way, numerical values were obtained that represented the amounts of cleaved and uncleaved DNAzyme molecules in the experiment.

| Sequences | | | |
|---|---|---|---|
| SEQ ID NO: 1 | DNA zyme consensus 3 | 5'-N$^{\&}$ G Y$^{\$}$ Y$^{\#}$ GT N$^{\$}$ Y$^{\#}$ ACGC Y$^{\#}$ Y$^{\$}$ YGTCTTATCGGTT Y$^{\$}$ Y$^{\$}$ N$^{\#}$ N-3', | 31 |
| SEQ ID NO: 2 | DNA zyme consensus 3a | 5'-N$^{\&}$ G Y$^{\$}$ Y# GT N$^{\$}$ Y$^{\#}$ ACGC Y$^{\#}$ Y$^{\$}$ YGTCTTATCGGTT Y$^{\$}$ N$^{\#}$ Y$^{\$}$ N$^{\#}$ N-3', | 32 |
| SL1 (SEQ ID NO: 3) | Sub-library 1 | CAGTAGACTAAGCACACTGATACAGATAATANNNNNNNNNNNNNNNN NNNNNNNNNNNNNNTATTATCTGACCTCTACCTCACCATC | 87 |
| SL2 (SEQ ID NO: 4) | Sub-library 2 | CAGTAGACTAAGCACACTGATACAGATAATTNNNNNNNNNNNNNNNN NNNNNNNNNNNNNNAATTATCTGACCTCTACCTCACCATC | 87 |
| SL3 (SEQ ID NO: 5) | Sub-library 3 | CAGTAGACTAAGCACACTGATACAGATAATCNNNNNNNNNNNNNNNN NNNNNNNNNNNNNNGATTATCTGACCTCTACCTCACCATC | 87 |
| SL4 (SEQ ID NO: 6) | Sub-library 4 | CAGTAGACTAAGCACACTGATACAGATAATGNNNNNNNNNNNNNNNN NNNNNNNNNNNNNNCATTATCTGACCTCTACCTCACCATC | 87 |
| WM1 (SEQ ID NO: 7) | Active fraction weight marker | Cy5-NNNNNNNNNNNNNNNNNNNNNNNNNNNNNNTATTATCTGACCTCTAC CTCACCATC | 56 |

-continued

| Sequences | | | |
|---|---|---|---|
| WM2 (SEQ ID NO: 19; SEQ ID NO: 20) | Extension weight marker | Cy5-TTTTTTTTTTTTTTTTTTTTTTTTTTTTTT-iSpC3-GATGGTGAGGTAGAGGTCAGATAATNNNNNNNNNNNNNNNNNNNNNNNNNNNNNNN | 86 |
| WM3 (SEQ ID NO: 19; SEQ ID NO: 21) | Ligation weight marker | Cy5-TTTTTTTTTTTTTTTTTTTTTTTTTTTTTT-iSpC3-GATGGTGAGGTAGAGGTCAGATAATNNNNNNNNNNNNNNNNNNNNNNNNNNNNNNNNATTATCTGTATCAGTGTGCTTAGTCTACTG | 117 |
| WM4 (SEQ ID NO: 8) | PCR weight marker | Cy3-CAGTAGACTAAGCACACTGATACAGATAATNNNNNNNNNNNNNNNNNNNNNNNNNNNNNNNNATTATCTGACCTCTACCTCACCATC | 87 |
| P1 (SEQ ID NO: 22; SEQ ID NO: 23) | Extension/PCR reverse primer | Cy5-TTTTTTTTTTTTTTTTTTTTTTTTT-iSpC3-GATGGTGAGGTAGAGGTCAGATAAT | 50 |
| P2 (SEQ ID NO: 9) | PCR forward primer | Cy3-CAGTAGACTAAGCACACTGATACAG | 25 |
| LA1 (SEQ ID NO: 10) | Ligation adaptor-N | p-NATTATCTGTATCAGTGTGCTTAGTCTACTG-3C6 | 31 |
| LA2 (SEQ ID NO: 11) | Ligation adaptor-A | p-AATTATCTGTATCAGTGTGCTTAGTCTACTG-3C6 | 31 |
| LA3 (SEQ ID NO: 12) | Ligation adaptor-T | p-TATTATCTGTATCAGTGTGCTTAGTCTACTG-3C6 | 31 |
| LA4 (SEQ ID NO: 13) | Ligation adaptor-C | p-CATTATCTGTATCAGTGTGCTTAGTCTACTG-3C6 | 31 |
| LA5 (SEQ ID NO: 14) | Ligation adaptor-G | p-GATTATCTGTATCAGTGTGCTTAGTCTACTG-3C6 | 31 |
| 12-35-DL (SEQ ID NO: 15) | Double labeled 12-35 | Cy3-TTTTTTTTGCAGATAATGGTCCGCCGTGTTAGGTGCGGGGTCGCTGTGGCATTATCT-Cy5 | 57 |
| 8-35-DL (SEQ ID NO: 16) | Double labeled 8-35 | Cy3-TTTTTTTTGCAGATAATCGGTACTAAAACAGTGGTGGGGGGGATCGCCACATTATCT-Cy5 | 57 |
| 12-11-DL (SEQ ID NO: 17) | Double labeled 12-11 | Cy3-TTTTTTTTGCAGATAATGGGTCGTGTACGCCTCGTCTTATCGGTTATCTATTATCT-Cy5 | 56 |

-continued

| Sequences | | | |
|---|---|---|---|
| 12-8-DL (SEQ ID NO: 18) | Double labeled 12-8 | Cy3-TTTTTTTTGCAGATAATCAGCTACAGCCTTTACCTCCGGTGCACGGACGTATTATCT-Cy5 | 57 |

| | | | |
|---|---|---|---|
| A cleavers | SEQ ID NO: 24 | RT-3-A | A\| GGTCGTTCACGCCTCGTCTTATCGGTTTTCA |
| | SEQ ID NO: 25 | RT-7-A | A\| GGTCGTTCACGCCTTGTCTTATCGGTTTTCA |
| | SEQ ID NO: 26 | RT-9-A | A\| GGTCGTTCACGCTTCGTCTTATCGGTTTTCA |
| | SEQ ID NO: 27 | RT-12-A | A\| TGTCGTTCACGCCTCGTCTTATCGGTTTTCA |
| | SEQ ID NO:28 | RT-15-A | A\| GGTCGTACACGCCTTGTCTTATCGGTTTTCA |
| | SEQ ID NO: 29 | RC-4-A | A\| GGTCGTTCACGCCTCGTCTTATCGGTTTTCG |
| | SEQ ID NO: 30 | RC-15-A | A\| GGTCGTTCACGCCTTGTCTTATCGGTTTTCG |
| T cleavers | SEQ ID NO: 31 | RT-7 | T\| GGTCGTTCACGCCTTGTCTTATCGGTTTTCA |
| | SEQ ID NO: 32 | RT-12 | T\| TGTCGTTCACGCCTCGTCTTATCGGTTTTCA |
| | SEQ ID NO: 33 | RC-5-T | T\| GGCTGTTCACGCCTTGTCTTATCGGTTTTCG |
| C cleavers | SEQ ID NO: 34 | RT-7-C | C\| GGTCGTTCACGCCTTGTCTTATCGGTTTTCA |
| | SEQ ID NO: 35 | RT-12-C | C\| TGTCGTTCACGCCTCGTCTTATCGGTTTTCA |
| | SEQ ID NO: 36 | RC-5 | C\| GGCTGTTCACGCCTTGTCTTATCGGTTTTCG |
| | SEQ ID NO: 37 | RC-15 | C\| GGTCGTTCACGCCTTGTCTTATCGGTTTTCG |
| G cleavers | SEQ ID NO: 38 | RT-3-G | G\| GGTCGTTCACGCCTCGTCTTATCGGTTTTCA |
| | SEQ ID NO: 39 | RT-7-G | G\| GGTCGTTCACGCCTTGTCTTATCGGTTTTCA |
| | SEQ ID NO: 40 | RT-9-G | G\| GGTCGTTCACGCTTCGTCTTATCGGTTTTCA |
| | SEQ ID NO: 41 | RT-15-G | G\| GGTCGTACACGCCTTGTCTTATCGGTTTTCA |
| | SEQ ID NO: 42 | RC-15-G | G\| GGTCGTTCACGCCTTGTCTTATCGGTTTTCG |
| | SEQ ID NO: 43 | RG-3 | G\| GGTCGTTCACGCCTTGTCTTATCGGTTCCTCC |
| | SEQ ID NO: 44 | RG-5 | G\| GGTCGTTCACGCCTCGTCTTATCGGTTTTCC |
| | SEQ ID NO: 45 | RG-8 | G\| GGTCGTTCACGCCTCGTCTTATCGGTTCCTCC |
| | SEQ ID NO: 46 | RG-11 | G\| GGTCGTTCACGCCTTGTCTTATCGGTTTTCC |
| | SEQ ID NO: 47 | 12-11 parent | GGTCGTGTACGCCTCGTCTTATCGGTTATCT |

iSpC3-internal C3 spacer modification (C3 is phosphoramidite),
3C6-3'-end blocking C6 spacer (C6 is a 6-carbon spacer),
Cy3-cyanine dye,
Cy5-cyanine dye,
A-a nucleotide with the base adenine,
C-a nucleotide with the base cytosine,
G-a nucleotide with the base guanine,
T-a nucleotide with the base thymidine,
N-independently A, C, G, or T,
Y-independently C or T,
$^{\$}$is independently preferably T,
$^{\#}$is independently preferably C,
$^{\&}$is independently preferably G.

The invention claimed is:

1. A single-stranded DNA strand comprising a self-cleaving DNAzyme,

Wherein the self-cleaving DNAzyme comprises a core sequence that comprises a polynucleotide sequence that is:

I. at least 80% identical to SEQ ID NO: 34; and

II. comprises a sequence: GTCTTATCGGTT set forth in SEQ ID NO: 48; and wherein the core sequence has a self-cleavage activity as determined by contacting the single-stranded DNA strand with a buffer that comprises $Mg^{2+}$, $Na^{+}$, $Zn^{2+}$, $Cu^{2+}$, $Mn^{2+}$, $Ca^{2+}$, or a combination thereof at 25° C. in an in vitro assay.

2. The single-stranded DNA strand of claim 1, wherein the core sequence comprises a polynucleotide sequence that is at least 90% identical to the polynucleotide sequence of SEQ ID NO: 34 and comprises the polynucleotide sequence: GTCTTATCGGTT set forth in SEQ ID NO: 48.

3. The single-stranded DNA strand of claim 1, wherein the core sequence comprises a sequence from any one of SEQ ID NOs 24-46.

4. The single-stranded DNA strand of claim 1, wherein the core sequence is a self-cleaving DNAzyme selected from the group consisting of: an A-cleaver that cleaves after an adenine, a T-cleaver that cleaves after thymine, a C-cleaver that cleaves after a cytosine, and a G-cleaver that cleaves after a guanine.

5. The single-stranded DNA strand of claim 1, wherein the core sequence self-cleaves with a final cleavage yield $Y_{max}$ of at least 90%, determined by the in vitro assay.

6. The single-stranded DNA strand of claim 1, wherein the self-cleavage activity of the core sequence is a hydrolytic cleavage.

7. The single-stranded DNA strand of claim 6, wherein the hydrolytic cleavage of the core sequence results in production of a single stranded DNA molecule.

8. The single-stranded DNA strand of claim 7, wherein the single stranded DNA molecule produced through the self-cleaving DNAzyme comprises reduced scars at the 5' and/or 3' end of single stranded DNA as compared to an amount of scars present in a single stranded DNA molecule generated from I-R3 DNAzyme.

9. The single-stranded DNA strand of claim 1 further comprises a first constant sequence and a second constant sequence that flank a 5' end and a 3' end of the core sequence, respectively.

10. The single-stranded DNA strand of claim 9, wherein the single-stranded DNA strand further comprises a cleavage site within the first constant sequence or between the first constant sequence and the core sequence.

11. The single-stranded DNA strand of claim 9, wherein the first constant sequence is different from the second constant sequence.

12. The single-stranded DNA strand of claim 9, wherein the first constant sequence and the second constant sequence have complementarity thereby forming a stem flanking the core sequence.

13. The single-stranded DNA strand of claim 6, wherein the hydrolytic cleavage of the single-stranded DNA strand results in a cleaved single-stranded molecule that is scar-free at the 3' end of the single-stranded molecule.

14. The single-stranded DNA strand of claim 1, wherein the core sequence has a length of about 30 to 40 nucleotides.

15. The single-stranded DNA strand of claim 6, wherein the self-cleavage activity is activated in the presence of a multivalent cation.

16. The single-stranded DNA strand of claim 1, wherein the self-cleaving DNAzyme comprises a sequence: 5'-$N^{\&}$ G $Y^{\$}$ $Y^{\#}$ GT $N^{\$}$ $Y^{\#}$ ACGC $Y^{\#}$ $Y^{\$}$ YGTCTTATCGGTT $Y^{\$}$ $Y^{\$}$ $N^{\#}$ N-3' set forth in SEQ ID NO 1, wherein A is a nucleotide with the base adenine, C is a nucleotide with the base cytosine, G is a nucleotide with the base guanine, T is a nucleotide with the base thymidine, N, $N^{\$}$, $N^{\&}$, or $N^{\#}$ is independently A, C, G, or T, and $Y^{\$}$ or $Y^{\#}$ is independently T or C.

17. The single-stranded DNA strand of claim 16, wherein $N^{\&}$ is G, $Y^{\$}$, or $N^{\$}$ is T, and Y or $N^{\#}$ is C.

18. The single-stranded DNA strand of claim 1, wherein the self-cleaving DNAzyme comprises a sequence: 5'-$N^{\&}$ G $Y_{\$}Y^{\#}$ GT $N^{\$}$ $Y^{\#}$ ACGC $Y^{\#}$ $Y^{\$}$ YGTCTTATCGGTT $Y^{\$}$ $N^{\#}$ $Y^{\$}$ $N^{\#}$ N-3' set forth in SEQ ID NO 2, wherein A is a nucleotide with the base adenine, C is a nucleotide with the base cytosine, G is a nucleotide with the base guanine, T is a nucleotide with the base thymidine, N, $N^{\$}$, $N^{\&}$, or $N^{\#}$ is independently A, C, G, or T, and Y or $Y^{V}$ is independently T or C.

19. The single-stranded DNA strand of claim 18, wherein $N^{\&}$ is G, $Y^{\$}$, or N$ is T, and $Y^{\#}$ or $N^{\#}$ is C.

* * * * *

SEQUENCE LISTING

```
Sequence total quantity: 48
SEQ ID NO: 1           moltype = DNA  length = 31
FEATURE                Location/Qualifiers
source                 1..31
                       mol_type = other DNA
                       organism = synthetic construct
misc_difference        30
                       note = N at position 30 may be present or absent
SEQUENCE: 1
ngyygtnyac gcyyygtctt atcggttyyn n                                 31

SEQ ID NO: 2           moltype = DNA  length = 32
FEATURE                Location/Qualifiers
source                 1..32
                       mol_type = other DNA
                       organism = synthetic construct
misc_difference        31
                       note = N at position 31 may be present or absent
SEQUENCE: 2
ngyygtnyac gcyyygtctt atcggttyny nn                                32

SEQ ID NO: 3           moltype = DNA  length = 87
FEATURE                Location/Qualifiers
source                 1..87
                       mol_type = other DNA
                       organism = synthetic construct
SEQUENCE: 3
cagtagacta agcacactga tacagataat annnnnnnnn nnnnnnnnnn nnnnnnnnnn  60
ntattatctg acctctacct caccatc                                      87

SEQ ID NO: 4           moltype = DNA  length = 87
FEATURE                Location/Qualifiers
source                 1..87
                       mol_type = other DNA
                       organism = synthetic construct
SEQUENCE: 4
cagtagacta agcacactga tacagataat tnnnnnnnnn nnnnnnnnnn nnnnnnnnnn  60
naattatctg acctctacct caccatc                                      87

SEQ ID NO: 5           moltype = DNA  length = 87
FEATURE                Location/Qualifiers
source                 1..87
                       mol_type = other DNA
                       organism = synthetic construct
SEQUENCE: 5
cagtagacta agcacactga tacagataat cnnnnnnnnn nnnnnnnnnn nnnnnnnnnn  60
ngattatctg acctctacct caccatc                                      87

SEQ ID NO: 6           moltype = DNA  length = 87
FEATURE                Location/Qualifiers
source                 1..87
                       mol_type = other DNA
                       organism = synthetic construct
SEQUENCE: 6
cagtagacta agcacactga tacagataat gnnnnnnnnn nnnnnnnnnn nnnnnnnnnn  60
ncattatctg acctctacct caccatc                                      87

SEQ ID NO: 7           moltype = DNA  length = 56
FEATURE                Location/Qualifiers
source                 1..56
                       mol_type = other DNA
                       organism = synthetic construct
misc_feature           1
                       note = 5' end linked to Cy5 cyanine dye
SEQUENCE: 7
nnnnnnnnnn nnnnnnnnnn nnnnnnnnnn tattatctga cctctacctc accatc      56

SEQ ID NO: 8           moltype = DNA  length = 87
FEATURE                Location/Qualifiers
source                 1..87
                       mol_type = other DNA
                       organism = synthetic construct
misc_feature           1
                       note = 5' end linked to Cy3 cyanine dye
SEQUENCE: 8
cagtagacta agcacactga tacagataat nnnnnnnnnn nnnnnnnnnn nnnnnnnnnn  60
nnattatctg acctctacct caccatc                                      87
```

-continued

```
SEQ ID NO: 9           moltype = DNA  length = 25
FEATURE                Location/Qualifiers
source                 1..25
                       mol_type = other DNA
                       organism = synthetic construct
misc_feature           1
                       note = 5' end linked to Cy3 cyanine dye
SEQUENCE: 9
cagtagacta agcacactga tacag                                        25

SEQ ID NO: 10          moltype = DNA  length = 31
FEATURE                Location/Qualifiers
source                 1..31
                       mol_type = other DNA
                       organism = synthetic construct
misc_feature           1
                       note = 5' end phosphorylated
misc_feature           31
                       note = 3' end blocking C6 spacer 3C6 (C6 is a 6-carbon
                        spacer)
SEQUENCE: 10
nattatctgt atcagtgtgc ttagtctact g                                 31

SEQ ID NO: 11          moltype = DNA  length = 31
FEATURE                Location/Qualifiers
source                 1..31
                       mol_type = other DNA
                       organism = synthetic construct
misc_feature           1
                       note = 5' end phosphorylated
misc_feature           31
                       note = 3' end blocking C6 spacer 3C6 (C6 is a 6-carbon
                        spacer)
SEQUENCE: 11
aattatctgt atcagtgtgc ttagtctact g                                 31

SEQ ID NO: 12          moltype = DNA  length = 31
FEATURE                Location/Qualifiers
source                 1..31
                       mol_type = other DNA
                       organism = synthetic construct
misc_feature           1
                       note = 5' end phosphorylated
misc_feature           31
                       note = 3' end blocking C6 spacer 3C6 (C6 is a 6-carbon
                        spacer)
SEQUENCE: 12
tattatctgt atcagtgtgc ttagtctact g                                 31

SEQ ID NO: 13          moltype = DNA  length = 31
FEATURE                Location/Qualifiers
source                 1..31
                       mol_type = other DNA
                       organism = synthetic construct
misc_feature           1
                       note = 5' end phosphorylated
misc_feature           31
                       note = 3' end blocking C6 spacer 3C6 (C6 is a 6-carbon
                        spacer)
SEQUENCE: 13
cattatctgt atcagtgtgc ttagtctact g                                 31

SEQ ID NO: 14          moltype = DNA  length = 31
FEATURE                Location/Qualifiers
source                 1..31
                       mol_type = other DNA
                       organism = synthetic construct
misc_feature           1
                       note = 5' end phosphorylated
misc_feature           31
                       note = 3' end blocking C6 spacer 3C6 (C6 is a 6-carbon
                        spacer)
SEQUENCE: 14
gattatctgt atcagtgtgc ttagtctact g                                 31

SEQ ID NO: 15          moltype = DNA  length = 57
FEATURE                Location/Qualifiers
source                 1..57
                       mol_type = other DNA
```

```
                        organism = synthetic construct
misc_feature            1
                        note = 5' end linked to Cy3 cyanine dye
misc_feature            57
                        note = 3' end linked to Cy5 cyanine dye
SEQUENCE: 15
ttttttttgc agataatggt ccgccgtgtt aggtgcgggg tcgctgtggc attatct     57

SEQ ID NO: 16           moltype = DNA  length = 57
FEATURE                 Location/Qualifiers
source                  1..57
                        mol_type = other DNA
                        organism = synthetic construct
misc_feature            1
                        note = 5' end linked to Cy3 cyanine dye
misc_feature            57
                        note = 3' end linked to Cy5 cyanine dye
SEQUENCE: 16
ttttttttgc agataatcgg tactaaaaca gtggtgggcg ggatcgccac attatct     57

SEQ ID NO: 17           moltype = DNA  length = 56
FEATURE                 Location/Qualifiers
source                  1..56
                        mol_type = other DNA
                        organism = synthetic construct
misc_feature            1
                        note = 5' end linked to Cy3 cyanine dye
misc_feature            56
                        note = 3' end linked to Cy5 cyanine dye
SEQUENCE: 17
ttttttttgc agataatggg tcgtgtacgc ctcgtcttat cggttatcta ttatct      56

SEQ ID NO: 18           moltype = DNA  length = 57
FEATURE                 Location/Qualifiers
source                  1..57
                        mol_type = other DNA
                        organism = synthetic construct
misc_feature            1
                        note = 5' end linked to Cy3 cyanine dye
misc_feature            57
                        note = 3' end linked to Cy5 cyanine dye
SEQUENCE: 18
ttttttttgc agataatcag ctacagcctt tacctccggt gcacggacgt attatct     57

SEQ ID NO: 19           moltype = DNA  length = 30
FEATURE                 Location/Qualifiers
source                  1..30
                        mol_type = other DNA
                        organism = synthetic construct
misc_feature            1
                        note = 5' end linked to Cy5 cyanine dye
misc_feature            30
                        note = 3' end linked to internal C3 spacer modification
                         iSpC3 (C3 is phosphoramidite)
SEQUENCE: 19
tttttttttt tttttttttt tttttttttt                                   30

SEQ ID NO: 20           moltype = DNA  length = 56
FEATURE                 Location/Qualifiers
source                  1..56
                        mol_type = other DNA
                        organism = synthetic construct
misc_feature            1
                        note = 5' end linked to internal C3 spacer modification
                         iSpC3 (C3 is phosphoramidite)
SEQUENCE: 20
gatggtgagg tagaggtcag ataatnnnnn nnnnnnnnnn nnnnnnnnnn nnnnnn      56

SEQ ID NO: 21           moltype = DNA  length = 87
FEATURE                 Location/Qualifiers
source                  1..87
                        mol_type = other DNA
                        organism = synthetic construct
misc_feature            1
                        note = 5' end linked to internal C3 spacer modification
                         iSpC3 (C3 is phosphoramidite)
SEQUENCE: 21
gatggtgagg tagaggtcag ataatnnnnn nnnnnnnnnn nnnnnnnnnn nnnnnnnatt  60
atctgtatca gtgtgcttag tctactg                                      87
```

```
SEQ ID NO: 22          moltype = DNA  length = 25
FEATURE                Location/Qualifiers
source                 1..25
                       mol_type = other DNA
                       organism = synthetic construct
misc_feature           25
                       note = 3' end linked to internal C3 spacer modification
                        iSpC3 (C3 is phosphoramidite)
misc_feature           1
                       note = 5' end linked to Cy5 cyanine dye
SEQUENCE: 22
tttttttttt tttttttttt ttttt                                        25

SEQ ID NO: 23          moltype = DNA  length = 25
FEATURE                Location/Qualifiers
source                 1..25
                       mol_type = other DNA
                       organism = synthetic construct
misc_feature           1
                       note = 5' end linked to internal C3 spacer modification
                        iSpC3 (C3 is phosphoramidite)
SEQUENCE: 23
gatggtgagg tagaggtcag ataat                                        25

SEQ ID NO: 24          moltype = DNA  length = 31
FEATURE                Location/Qualifiers
source                 1..31
                       mol_type = other DNA
                       organism = synthetic construct
SEQUENCE: 24
ggtcgttcac gcctcgtctt atcggttttc a                                 31

SEQ ID NO: 25          moltype = DNA  length = 31
FEATURE                Location/Qualifiers
source                 1..31
                       mol_type = other DNA
                       organism = synthetic construct
SEQUENCE: 25
ggtcgttcac gccttgtctt atcggttttc a                                 31

SEQ ID NO: 26          moltype = DNA  length = 31
FEATURE                Location/Qualifiers
source                 1..31
                       mol_type = other DNA
                       organism = synthetic construct
SEQUENCE: 26
ggtcgttcac gcttcgtctt atcggttttc a                                 31

SEQ ID NO: 27          moltype = DNA  length = 31
FEATURE                Location/Qualifiers
source                 1..31
                       mol_type = other DNA
                       organism = synthetic construct
SEQUENCE: 27
tgtcgttcac gcctcgtctt atcggttttc a                                 31

SEQ ID NO: 28          moltype = DNA  length = 31
FEATURE                Location/Qualifiers
source                 1..31
                       mol_type = other DNA
                       organism = synthetic construct
SEQUENCE: 28
ggtcgtacac gccttgtctt atcggttttc a                                 31

SEQ ID NO: 29          moltype = DNA  length = 31
FEATURE                Location/Qualifiers
source                 1..31
                       mol_type = other DNA
                       organism = synthetic construct
SEQUENCE: 29
ggtcgttcac gcctcgtctt atcggttttc g                                 31

SEQ ID NO: 30          moltype = DNA  length = 31
FEATURE                Location/Qualifiers
source                 1..31
                       mol_type = other DNA
                       organism = synthetic construct
SEQUENCE: 30
```

```
ggtcgttcac gccttgtctt atcggttttc g                                31

SEQ ID NO: 31          moltype = DNA  length = 31
FEATURE                Location/Qualifiers
source                 1..31
                       mol_type = other DNA
                       organism = synthetic construct
SEQUENCE: 31
ggtcgttcac gccttgtctt atcggttttc a                                31

SEQ ID NO: 32          moltype = DNA  length = 31
FEATURE                Location/Qualifiers
source                 1..31
                       mol_type = other DNA
                       organism = synthetic construct
SEQUENCE: 32
tgtcgttcac gcctcgtctt atcggttttc a                                31

SEQ ID NO: 33          moltype = DNA  length = 31
FEATURE                Location/Qualifiers
source                 1..31
                       mol_type = other DNA
                       organism = synthetic construct
SEQUENCE: 33
ggctgttcac gccttgtctt atcggttttc g                                31

SEQ ID NO: 34          moltype = DNA  length = 31
FEATURE                Location/Qualifiers
source                 1..31
                       mol_type = other DNA
                       organism = synthetic construct
SEQUENCE: 34
ggtcgttcac gccttgtctt atcggttttc a                                31

SEQ ID NO: 35          moltype = DNA  length = 31
FEATURE                Location/Qualifiers
source                 1..31
                       mol_type = other DNA
                       organism = synthetic construct
SEQUENCE: 35
tgtcgttcac gcctcgtctt atcggttttc a                                31

SEQ ID NO: 36          moltype = DNA  length = 31
FEATURE                Location/Qualifiers
source                 1..31
                       mol_type = other DNA
                       organism = synthetic construct
SEQUENCE: 36
ggctgttcac gccttgtctt atcggttttc g                                31

SEQ ID NO: 37          moltype = DNA  length = 31
FEATURE                Location/Qualifiers
source                 1..31
                       mol_type = other DNA
                       organism = synthetic construct
SEQUENCE: 37
ggtcgttcac gccttgtctt atcggttttc g                                31

SEQ ID NO: 38          moltype = DNA  length = 31
FEATURE                Location/Qualifiers
source                 1..31
                       mol_type = other DNA
                       organism = synthetic construct
SEQUENCE: 38
ggtcgttcac gcctcgtctt atcggttttc a                                31

SEQ ID NO: 39          moltype = DNA  length = 31
FEATURE                Location/Qualifiers
source                 1..31
                       mol_type = other DNA
                       organism = synthetic construct
SEQUENCE: 39
ggtcgttcac gccttgtctt atcggttttc a                                31

SEQ ID NO: 40          moltype = DNA  length = 31
FEATURE                Location/Qualifiers
source                 1..31
                       mol_type = other DNA
                       organism = synthetic construct
```

```
SEQUENCE: 40
ggtcgttcac gcttcgtctt atcggttttc a                                      31

SEQ ID NO: 41          moltype = DNA  length = 31
FEATURE                Location/Qualifiers
source                 1..31
                       mol_type = other DNA
                       organism = synthetic construct
SEQUENCE: 41
ggtcgtacac gccttgtctt atcggttttc a                                      31

SEQ ID NO: 42          moltype = DNA  length = 31
FEATURE                Location/Qualifiers
source                 1..31
                       mol_type = other DNA
                       organism = synthetic construct
SEQUENCE: 42
ggtcgttcac gccttgtctt atcggttttc g                                      31

SEQ ID NO: 43          moltype = DNA  length = 32
FEATURE                Location/Qualifiers
source                 1..32
                       mol_type = other DNA
                       organism = synthetic construct
SEQUENCE: 43
ggtcgttcac gccttgtctt atcggttcct cc                                     32

SEQ ID NO: 44          moltype = DNA  length = 31
FEATURE                Location/Qualifiers
source                 1..31
                       mol_type = other DNA
                       organism = synthetic construct
SEQUENCE: 44
ggtcgttcac gcctcgtctt atcggttttc c                                      31

SEQ ID NO: 45          moltype = DNA  length = 32
FEATURE                Location/Qualifiers
source                 1..32
                       mol_type = other DNA
                       organism = synthetic construct
SEQUENCE: 45
ggtcgttcac gcctcgtctt atcggttcct cc                                     32

SEQ ID NO: 46          moltype = DNA  length = 31
FEATURE                Location/Qualifiers
source                 1..31
                       mol_type = other DNA
                       organism = synthetic construct
SEQUENCE: 46
ggtcgttcac gccttgtctt atcggttttc c                                      31

SEQ ID NO: 47          moltype = DNA  length = 31
FEATURE                Location/Qualifiers
source                 1..31
                       mol_type = other DNA
                       organism = synthetic construct
SEQUENCE: 47
ggtcgtgtac gcctcgtctt atcggttatc t                                      31

SEQ ID NO: 48          moltype = DNA  length = 12
FEATURE                Location/Qualifiers
source                 1..12
                       mol_type = other DNA
                       organism = synthetic construct
SEQUENCE: 48
gtcttatcgg tt                                                           12
```